(12) United States Patent
Vriezen et al.

(10) Patent No.: US 10,694,696 B2
(45) Date of Patent: Jun. 30, 2020

(54) *CITRULLUS LANATUS* PRODUCING FRUITS WITH HIGH TEXTURE FRUIT FLESH

(71) Applicant: NUNHEMS B.V., Nunhem (NL)

(72) Inventors: Hendrik Willem Vriezen, Haelen (NL); Alberto Sirizzotti, Sant'Agata Bolognese (IT)

(73) Assignee: NUNHEMS B.V., Nunhem (NL)

(*) Notice: Subject to any disclaimer, the term of this patent is extended or adjusted under 35 U.S.C. 154(b) by 0 days.

(21) Appl. No.: 15/543,860

(22) PCT Filed: Jan. 14, 2016

(86) PCT No.: PCT/EP2016/050617
§ 371 (c)(1),
(2) Date: Jul. 14, 2017

(87) PCT Pub. No.: WO2016/113329
PCT Pub. Date: Jul. 21, 2016

(65) Prior Publication Data
US 2018/0049384 A1    Feb. 22, 2018

(30) Foreign Application Priority Data

Jan. 15, 2015 (EP) .................................... 15151329
May 12, 2015 (EP) .................................... 15167355

(51) Int. Cl.
*A01H 6/34* (2018.01)
*C07K 14/415* (2006.01)
*A01H 5/08* (2018.01)

(52) U.S. Cl.
CPC ............... *A01H 6/342* (2018.05); *A01H 5/08* (2013.01); *C07K 14/415* (2013.01)

(58) Field of Classification Search
CPC .................................. A01H 5/08; A01H 6/342
See application file for complete search history.

(56) References Cited

U.S. PATENT DOCUMENTS

| 2003/0172412 | A1  | 9/2003  | Zhang et al. |             |
|--------------|-----|---------|--------------|-------------|
| 2003/0217394 | A1  | 11/2003 | Zhang        |             |
| 2004/0060085 | A2  | 3/2004  | Zhang et al. |             |
| 2006/0005284 | A1* | 1/2006  | Tolla ........................ | A01H 5/08 800/308 |
| 2013/0055466 | A1* | 2/2013  | Juarez ...................... | A01H 5/08 800/266 |

FOREIGN PATENT DOCUMENTS

| EP | 2443919 A2     | 4/2012 |
|----|----------------|--------|
| WO | WO 03/075641 A2 | 9/2003 |
| WO | WO 2006/014463 A2 | 2/2006 |
| WO | WO 2012/069539 A1 | 5/2012 |
| WO | WO 2013/033611 A1 | 3/2013 |

OTHER PUBLICATIONS

European Search Report issued in European Patent Application No. 15151329 dated Jun. 8, 2015 (7 pages).
Guner et al., "The Genes of Watermelon", Hort Science, 2004, vol. 39, No. 6, pp. 1175-1182.
Henikoff et al., "Amino Acid Substitution Matrices from Protein Blocks", Proc. Natl. Acad. Sci., 1992, vol. 89, pp. 10915-10919.
International Search Report and Written Opinion issued in International Patent Application No. PCT/EP2016/050617, dated Mar. 17, 2016 (13 pages).
Kumar et al., "Predicting the effects of coding non-synonymous variants on protein function using the SIFT algorithm", Nature Protocols 2009, vol. 4, No. 8, pp. 1073-1082.
Levi et al., "An Extended Genetic Linkage Map for Watermelon Based on a Testcross and a BC2F2 Population", American Journal of Plant Sciences, 2008, vol. 2, pp. 93-110.
Sandlin., "Genetic Mapping in *Citrullus Lanatus*", Thesis, pp. 1-94, 2010.
Sari et al., "Comparison of ploidy level screening methods in watermelon: *Citrullus lanatus* (Thunb.) Matsum. And Nakai", Scientia Horticulturae, 1999, vol. 82, pp. 265-277.
Wehner et al., "Breeding and Seed Production", in: "Watermelons: Characteristics, production, and marketing", 2001, ASHS Press, pp. 27-73.
Wolukau et al., "Identification of Amplified Fragment Length Polymorphism Markers Linked to Gummy Stem Blight (*Didymella bryoniae*) Resistance in Melon (*Cucumis melo* L.) PI 420145", HortScience, 2009, vol. 4, No. 1, pp. 32-34.

* cited by examiner

*Primary Examiner* — Lee A Visone
(74) *Attorney, Agent, or Firm* — Arent Fox LLP

(57) ABSTRACT

The invention relates to a cultivated plant of the species *Citrullus lanatus* var. *lanatus* (watermelon) producing fruits with high texture fruit flesh, wherein the plant optionally is a diploid, triploid or tetraploid plant. In one aspect, the plant of the invention comprises one or more mutations in the C1MBP 17_2 allele encoding a mutant C1MBP 17_2 protein or encoding lower levels of wild type C1MPBP 17_2 protein compared to wild type plants.

16 Claims, 8 Drawing Sheets
Specification includes a Sequence Listing.

Figure 1

```
# Aligned_sequences: 2
# 1: WT ClMBP 17_2 protein
# 2: mutant ClMBP 17_2 protein
# Matrix: EBLOSUM62
# Gap_penalty: 10.0
# Extend_penalty: 0.5

# Length: 227
# Identity:     226/227 (99.6%)
# Similarity:   226/227 (99.6%)
# Gaps:           0/227 ( 0.0%)
# Score: 1125.0

#=======================================

WT         1 MGRGKIEIKRIENTTNRQVTFCKRRNGLLKKAYELSVLCDAEVALIVFSS     50
                 |||||||||||||||||||||||||||||||||||.||||||||||||||
    mutant     1 MGRGKIEIKRIENTTNRQVTFCKRRNGLLKKAYELFVLCDAEVALIVFSS     50
```

```
WT       51 RGRLYEYSNNSIKTTIERYKKACSDSSATSSVTELI
            ||||||||||||||||||||||||||||||||||||
mutant   51 RGRLYEYSNNSIKTTIERYKKACSDSSATSSVTELI WT      101 IQMLQNSNSNLVRHLMGDSLSALTVKELKQLENRLI
            |||||||||||||||||||||||||||||||||||||||||||||||||
mutant  101 IQMLQNSNSNLVRHLMGDSLSALTVKELKQLENRLERGITRIRSKKHEML    150

WT      151 LAEIEYLQKREIELENENVCIRTKIAEVERLQQANMVSGQELNAIQALAS    200
            |||||||||||||||||||||||||||||||||||||||||||||||||
mutant  151 LAEIEYLQKREIELENENVCIRTKIAEVERLQQANMVSGQELNAIQALAS    200

WT      201 RNFFSPNMMEGGAVTYSHQDKKMLHIG    227
            ||||||||||||||||||||||||||
mutant  201 RNFFSPNMMEGGAVTYSHQDKKMLHIG    227
```

A

B

A

B

A

B

A

B

CITRULLUS LANATUS PRODUCING FRUITS WITH HIGH TEXTURE FRUIT FLESH

CROSS REFERENCE TO RELATED APPLICATIONS

This application is a 35 U.S.C. 371 National Phase of PCT Application No. PCT/EP2016/050617 filed Jan. 14, 2016, which claims benefit to EP Application No. 15151329.8 filed Jan. 15, 2015, and EP Application No. 15167355.5 filed May 12, 2015, the disclosure of each of which is hereby incorporated by reference in its entirety.

The present invention relates to the field of plant breeding. In particular to the field of breeding of *Citrullus lanatus* (watermelon). Provided are *Citrullus lanatus* plants producing fruits with a high texture fruit flesh. Further, methods for producing watermelon plants producing such fruits with high texture fruit flesh are provided herein together with plants obtained in such methods.

In a further aspect the invention provides seeds, parts and fruits from such plants. Also provided is the use of the gene and markers for the identification of the high texture fruit phenotype in *Citrullus lanatus*.

BACKGROUND

Watermelon, *Citrullus lanatus* (Thunb.) Matsum. & Nakai (2n=2x=22), belongs to the botanical family Cucurbitaceae. It is an important specialty crop accounting for 7% of the world area devoted to vegetable crops.

The goal of vegetable breeding is to combine various desirable traits in a single variety/hybrid. Such desirable traits may include greater yield, resistance to insects or pests, tolerance to heat and drought, desired earliness, seedlessness, better agronomic quality, higher nutritional value, growth rate, fruit flesh quality and fruit properties.

Cultivated watermelon (*Citrullus lanatus* var. *lanatus*) is a member of the Cucurbitaceae family. The plant is a large and sprawling annual, grown for its fruit. The fruit flesh is commonly red. Diploid watermelon fruits contain black seeds, which are considered undesirable for certain uses. Triploid watermelon fruits, produced by pollinating triploid plants with diploid pollen of pollenizer plants, are seedless.

Many different watermelon cultivars have been produced, and watermelon breeding efforts have been underway in many parts of the world. Some breeding objectives include varying the color, texture and flavor of the fruit, and absence of seeds. Other objectives include disease or pest resistance, optimizing flesh thickness, yield, suitability to various climatic circumstances, solid content (% dry matter), and sugar content.

The market for fresh-cut watermelon has increased at a rate of 10-30% annually for the last decade and the fresh-cut product now accounts for 13% of total fresh cut sales (USA). Fresh-cut watermelon is marketed as halves, quarters and slices with rinds, or as rind-free chunks. Quality degradation has been associated with decreased acceptability of texture, color and sweetness, with shelf-life limited by water soaking, juice leakage, off-odor development and increased microbial growth and spoilage.

The advantage of fresh-cut watermelon displays is that consumers can visually assess the quality of the product. Overripe fruits may show signs of decay, while unripe fruits are not uniform in fruit flesh pigmentation. Juice leakage is also a parameter that is associated with decaying fruit freshness.

Cutting watermelon fruits is known to have an impact on fruit quality by softening or deterioration of the fruit flesh causing liquid leakage. Cutting watermelons therefor has a negative impact on the shelf life of the fresh cut watermelon fruit.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different varieties produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

Watermelon fruit firmness is described in EP2443919 (Seminis Vegetable Seeds). EP2443919 discloses that there are no industry standards to describe the firmness of the edible portions of watermelon fruits. This has led to a wide range of descriptors in use, from "firm" and "crisp" (Erma Zaden catalog descriptors for varieties Gil 104 and Erma 12) to "very firm flesh" (Zhang et al. in USPTO application numbers 20040060085 and 20030217394 and Seminis watermelon catalog for the variety Cooperstown). Seminis has described cultivars Fenway, Royal Star and Sentinel as having "excellent crispness," "firm flesh" and "crisp juicy flesh," respectively. In addition, Rogers Seed Company advertises the Tri-X Brand 626 as "exceptionally firm" and the Tri-X Brand 313 as having "firm texture" and "crispness."

Despite the difference in language used in advertisings, EP2443919 discloses that quantitative measurements show that typical commercial germplasm has substantially lower flesh firmness than the watermelon fruit of EP2443919. EP2443919 further discloses that measurements of the prior art can be confusing, commercial watermelon lines produced prior to EP2443919 have fruit firmness that is well below 3 lbf and that the fruit of such commercial watermelon lines, once cut, undergo significant liquid leakage.

EP2443919 (also published as WO2006 014463, EP1765059 and US2006/005284) however, does not disclose the genetics causing the firmness of the watermelon fruit. EP2443919 suggests that firm flesh variation is the result of polygenic inheritance caused by several quantitative trait loci (QTLs). Variation in the phenotype of a quantitative trait is the result of the allelic composition at the QTLs and an environmental effect. Various potential causes for the variation are disclosed: (1) the fruit firmness trait may be controlled by several to many QTLs; (2) the fruit firmness trait may be caused by one or a few genes, but have a low heritability; and (3) the trait may be both polygenic and have low heritability. The QTLs of EP2443919 originate from a wild South African accession, PI296341, of *C. lanatus* var. *citroides*, which has small white fruits.

US2013/055466 (also published as WO2013033611, EP2750495) discloses a watermelon plant comprising at least one ultra-firm watermelon flesh phenotype wherein the locus is in a genomic region flanked by loci NW0251464 and NW0250266. According to FIG. 3A this locus is located on chromosome 9, though comparison of the marker loci NW0251464 and NW0250266 with the watermelon genome, suggests the locus is located on chromosome 6. The QTL also is an introgression from the same wild accession, PI296341, as mentioned above.

It is evident that the utility of an invention (in this case a specific trait in plant breeding such as fruit firmness) is higher when the trait can easily be transferred from one plant to another within the same species. A lower number of QTLs or one major QTL responsible for a specific trait is therefore preferred by plant breeders. Especially preferred are traits (e.g. plant phenotype characteristics) that are caused by a single gene. Traits caused by a mutation in a single endogenous gene of a cultivated plant (i.e. in cultivated germplasm of *C. lanatus* var. *lanatus*) has great advantages over QTLs identified in wild germplasm, such as PI296341 (*C. lanatus* var. *citroides*), because introgressions of QTLs from wild germplasm are very laborious and normally undesirable genetic regions are co-transferred into the cultivated germplasm together with the QTLs.

There is thus a need for watermelon plants that produce watermelon fruits that have an high texture (firm) fruit flesh, especially caused by one or more mutations in a single endogenous *C. lanatus* var. *lanatus* gene, and not by introgressions from wild germplasm, such as *C. lanatus* var. *citroides*. Thus, a mutation in an endogenous gene is herein referred to as a mutation in a gene of cultivated watermelon.

It is an object of the invention to provide a genetic cause for the high texture phenotype in cultivated watermelon (*C. lanatus* var. *lanatus*). The gene responsible for high texture (high texture gene) in cultivated watermelon was named ClMBP 17_2, for (*Citrullus lanatus* Mads Box Protein 17_2). It is also an object to provide cultivated watermelon plants, which produce fruits having an high texture fruit phenotype, conferred by one or more mutations in the endogenous (*C. lanatus* var. *lanatus*) high texture gene ClMBP 17_2, whereby said mutations lead to a reduced expression of the gene (and reduced levels of the encoded protein), or a reduced function or activity of the encoded protein. It is a further object to develop one or more markers that can be used in the selection of plants comprising one or more mutations in the high texture gene, resulting in a high texture phenotype. Also methods for either generating or for identifying plants or plant parts comprising alleles of the gene conferring the high texture fruit phenotype are provided.

SUMMARY OF THE INVENTION

The invention thus relates to a cultivated plant of the species *Citrullus lanatus* var. *lanatus* (watermelon) producing fruits with high texture fruit flesh at commercial maturity, wherein the plant optionally is a diploid, triploid or tetraploid plant. In one aspect, the plant of the invention produces (edible) fruits that have a fruit flesh firmness at the center (central column) of transversally cut-in-halves fruits that is at least 3.50 kg, preferably at least 3.75, 4.0, 4.2, 4.4, 4.5, 4.6, 4.8, 5.0, 5.2, 5.4, 5.6, 5.7, 5.8, 5.9, 6.0, or even at least 6.1 kg when a tip of 9 mm diameter is inserted into the flesh to a depth of 20 mm. In another aspect, the plant of the invention comprises one or more mutations in the ClMBP 17_2 allele encoding a mutant ClMBP 17_2 protein or encoding lower levels of wild type (functional) ClMPBP 17_2 protein compared to wild type plants or compared to plants having the same genetics except for the one or more mutations in the ClMBP 17_2 allele.

Definitions

The verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one", e.g. "a plant" refers also to several cells, plants, etc. Similarly, "a fruit" or "a plant" also refers to a plurality of fruits and plants.

A "plant line" or "breeding line" refers to a plant and its progeny. As used herein, the term "inbred line" refers to a plant line which has been repeatedly selfed, as a result of this selfing, plants of an inbred line are nearly identical to each other in genotype and phenotype.

As used herein, the term endogenous high texture gene refers to a (human-induced) mutant of a gene naturally occurring in cultivated watermelon of the species *C. lanatus* var. *lanatus*, said (human-induced) mutant gene produces a mutant protein which has a "reduced-function" or "loss-of-function", or said mutant gene produces lower/reduced levels of such protein. An example of such high texture gene as part of the invention, is the *Citrullus lanatus* var. *lanatus* Mads Box Protein 17_2 (ClMBP 17_2). The wild type (non-mutated) form of this protein is shown in SEQ ID NO: 1.

As used herein, watermelon having "high texture" fruits, or "high texture" fruit flesh refers to a watermelon plant producing fruits that have firmer fruit flesh and/or reduced leakage of watermelon fruit parts and/or longer shelf-life of the whole fruits or of fruit parts and/or a firmer watermelon rind compared to wild type watermelon plants (i.e. diploid watermelon being homozygous for the wild type ClMBP 17_2 allele). The skilled person knows how to determine fruit flesh firmness, liquid leakage and shelf-life, which is also described herein further below. Rind firmness can be measured by using a penetrometer, as known to the skilled person.

As used herein, the term "plant" includes the whole plant or any parts or derivatives thereof, preferably having the same genetic makeup as the plant from which it is obtained, such as plant organs (e.g. harvested or non-harvested fruits, leaves, etc.), plant cells, plant protoplasts, plant cell- or tissue-cultures from which whole plants can be regenerated, plant calli, plant cell clumps, plant transplants, seeds from which the plant can be grown and seeds produced by the plant, seedlings, plant cells that are intact in plants, plant clones or micropropagations, or parts of plants, such as plant cuttings, embryos, pollen, ovules, fruits (e.g. harvested tissues or organs), flowers, leaves, clonally propagated plants, roots, stems, root tips, grafts (scions and/or root stocks) and the like. Also any developmental stage is included, such as seedlings, cuttings prior or after rooting, etc. As used herein, the term plant includes plant and plant parts comprising one or more of the mutant ClMBP 17_2 alleles and/or mutant ClMBP 17_2 proteins of the invention or reduced wild type ClMBP protein.

In another embodiment, the term plant part refers to plant cells, or plant tissues or plant organs; that comprise one or more of the mutant ClMBP 17_2 alleles and/or ClMBP 17_2 mRNA (cDNA) and/or mutant ClMBP 17_2 protein of the invention. In one aspect a plant part can grow into a plant and/or live on photosynthesis (i.e. synthesizing carbohydrate and protein from the inorganic substance, such as water, carbon dioxide and mineral salt). In another aspect, a plant part cannot grow into a plant and/or live on photosynthesis (i.e. synthesizing carbohydrate and protein from the inorganic substance, such as water, carbon dioxide and mineral salt).

A plant part can be propagating or non-propagating, for example a non-propagating plant cell in particular a non-propagating plant cell comprising in its genome the mutant C1MBP 17_2 allele of the invention as discloses herein is provided.

It is, thus, understood that herein a watermelon plant, such as a diploid plant (2n), a triploid plant (3n), or a tetraploid plant (4n), encompasses not only an ungrafted plant, but also a plant with a rootstock of a different plant, such as a gourd or squash rootstock, another watermelon rootstock, a transgenic rootstock, etc.

As used herein, the term "variety" or "cultivar" or "plant variety" means a plant grouping within a single botanical taxon of the lowest known rank, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of 1 locus or gene (or a series of phenotypical characteristics due to this single locus or gene), but which can otherwise differ from one another enormously as regards the other loci or genes The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous). Although the term "homozygous" is commonly only used for diploid organisms, it is herein also used for tetraploid watermelon plants and plant parts, having four identical alleles of the mutant C1MBP 17_2 allele, and triploid watermelon plants and plant parts, having three identical copies of the mutant C1MBP 17_2 allele. It is noted that triploid fruits produced by pollenating triploid plants (comprising three mutant C1MBP 17_2 alleles) are seedless and also comprise the three mutant alleles, irrespective of the diploid pollen used to pollinate the triploid plant (i.e. to initiate fruit set).

The term "locus" (loci plural) means a specific place or places or a site on a chromosome where for example a gene or genetic marker is found.

"Diploid plant" refers to a plant, vegetative plant part(s), or seed from which a diploid plant can be grown, having two sets of chromosome, designated herein as 2n.

"Triploid plant" refers to a plant, vegetative plant part(s), or seed from which a triploid plant can be grown, having three sets of chromosomes, designated herein as 3n.

"Tetraploid plant" refers to a plant, vegetative plant part(s), or seed from which a tetraploid plant can be grown, having four sets of chromosomes, designated herein as 4n.

Ploidy can be easily determined by chromosome counting or flow cytometry or other known methods (Sari et al. 1999, Scientia Horticulturae 82: 265-277, incorporated herein by reference).

Watermelon plants are known as diploid (2n=2x=22), triploid watermelon (2n=3x=33), tetraploids (2n=4x=44). The diploid watermelon plants are suitable as pollenizers in triploid watermelon (2n=3x=33) production.

"Pollenizer plant" or "pollenizer" refers to the (inbred or hybrid) diploid plant, or parts thereof (e.g. its pollen or scion), suitable as pollenizer for inducing fruit set on triploid plants. A pollenizer plant is, thus, able to lead to good fruit set (and good triploid fruit yield) of triploid plants, by producing an appropriate amount of pollen at the appropriate day-time and for an appropriate period of time, e.g. at least during peak flowering time of the triploid female plants. A good triploid fruit yield is, for example, a yield comparable to the yield obtainable when using Polimax (produced by Nunhems) as pollenizer.

"Male parent" refers to the pollenizer plant used as male parent for inducing fruit set and seed production on a tetraploid female parent, resulting in F1 hybrid triploid seeds. Both the male parent and the female parent are inbred so that each parent is nearly homozygous and stable.

"Female parent" or "tetraploid parent" refers to the plant which is pollinated with pollen of the male parent, leading to the production of fruits containing triploid seeds. The female parent is inbred so that it is nearly homozygous and stable.

"Hybrid triploid plant" or "F1 triploid" is a triploid plant grown from hybrid, triploid seed obtained from cross fertilizing a male diploid parent with a female tetraploid parent.

"Seedless fruit" are triploid fruit which contain no mature seeds. The fruit may contain one or more small, edible, white ovules.

The term "edible" is used herein to refer to fruits marketable for human consumption, especially fresh consumption. The fruits have at harvest at least good, preferably very good flavor properties (i.e. taste and odor). To have good flavor properties the fruits preferably have an average level of Total Soluble Solids (brix) of at least about 7.0% or more.

The term "marketable" especially in conjunction with fruit, is used herein to refer to fruits that are fit to be sold, especially for human consumption. Marketable fruits have at least good, preferably very good flavor properties (i.e. taste and odor). To have good flavor properties the fruits preferably have an average level of Total Soluble Solids (brix) of at least about 7.0% or more. Preferably, marketable fruits are uniform in fruit size and fruit color and fruit shape and taste when they come from the same plant line or variety.

"Maturity" refers to maturity of fruit development and indicates the optimal time for harvest. Generally, growers of skill in the art harvest fruit at its maximum sweetness and flavor intensity (commercial maturity or commercial ripening stage) or substantially near its maximum sweetness and flavor intensity (harvest maturity). In watermelon, the maturity comes associated with changes in rind appearance, flesh color and sugar content.

"Hybrid triploid plant" is a triploid plant grown from hybrid, triploid seed obtained from cross fertilizing a male diploid parent with a female tetraploid parent.

"Seedless fruit" are triploid fruit which contain no or few mature seeds. The fruit may contain one or more small, edible, white ovules. Plants which produce seedless fruit may herein be referred to as "seedless".

"Interplanting" refers to the combination of two or more types of seeds and/or transplants sown or transplanted on the same field, especially the sowing and/or transplanting of pollenizers in the same field as triploid hybrid plants (for seedless fruit production on the triploid plants and diploid fruit production on the pollenizer plants). For example, the pollenizer may either be planted in separate rows or interplanted with the triploid plants in the same row (e.g. in hills within each row). Pollenizers may also be planted in between rows of triploids. Also seeds of pollenizers and triploid hybrids may be mixed prior to seeding, resulting in random seeding. The transplants of the triploid hybrid plants and/or pollenizer plants may also comprise a rootstock of a different plant. Suitable rootstocks are known in the art. Also encompassed are methods where the triploid hybrid plant and the pollenizer plant are grafted together onto one rootstock.

"Planting" or "planted" refers to seeding (direct sowing) or transplanting seedlings (plantlets) into a field by machine or hand.

"Vegetative propagation" refers to propagation of plants from vegetative tissue, e.g. by in vitro propagation or grafting methods (using scions).

"Vegetative type" or "growth type" or "vine type" refers to the combination of growth characteristics of the vegetative parts of a plant line or variety, such as (average) internode length, (average) length of the main vine, (average) length of the shortest and longest branch, average number of primary branches, etc. Three vegetative types can be distinguished: The "normal/standard vine type", the "compact vine type" and an "intermediate vine type" between these two.

Throughout this document "average" and "mean" are used interchangeably and refer to the arithmetic mean.

The term "nucleic acid sequence" (or nucleic acid molecule) refers to a DNA or RNA molecule in single or double stranded form, particularly a DNA encoding a protein or protein fragment according to the invention. An "isolated nucleic acid sequence" refers to a nucleic acid sequence which is no longer in the natural environment from which it was isolated, e.g. the nucleic acid sequence in a bacterial host cell or in the plant nuclear or plastid genome.

The terms "protein" or "polypeptide" are used interchangeably and refer to molecules consisting of a chain of amino acids, without reference to a specific mode of action, size, 3-dimensional structure or origin. A "fragment" or "portion" of C1MBP 17_2 protein may thus still be referred to as a "protein". An "isolated protein" is used to refer to a protein which is no longer in its natural environment, for example in vitro or in a recombinant bacterial or plant host cell.

The term "gene" means a DNA sequence comprising a region (transcribed region), which is transcribed into an RNA molecule (e.g. an mRNA or an RNAi molecule) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites. A gene may be an endogenous gene (in the species of origin) or a chimeric gene (e.g. a transgene or cis-gene).

"Expression of a gene" refers to the process wherein a DNA region, which is operably linked to appropriate regulatory regions, particularly a promoter, is transcribed into an RNA, which is biologically active, i.e. which is capable of being translated into a biologically active protein or peptide (or active peptide fragment) or which is active itself (e.g. in posttranscriptional gene silencing or RNAi). The coding sequence may be in sense-orientation and encodes a desired, biologically active protein or peptide, or an active peptide fragment.

An "active protein" or "functional protein" is a protein which has protein activity as measurable in vitro, e.g. by an in vitro activity assay, and/or in vivo, e.g. by the phenotype conferred by the protein. A "wild type" protein is a fully functional protein, as present in the wild type plant. A "mutant protein" is herein a protein comprising one or more mutations in the nucleic acid sequence encoding the protein, whereby the mutation(s) results in (the mutant nucleic acid molecule encoding) a "reduced-function" or "loss-of-function" protein, as e.g. measurable in vivo, e.g. by the phenotype conferred by the mutant allele.

A "reduced function C1MBP 17_2 protein" or "reduced activity C1MBP 17_2 protein" refers to a mutant C1MBP 17_2 protein which has a reduced catalytic activity affecting the fruit flesh of ripe/edible watermelon fruits comprising such reduced function C1MBP 17_2 protein when the allele encoding the mutant protein is present in homozygous form in the watermelon plant, causing firmer fruit flesh and/or reduced leakage of watermelon fruit parts and/or longer shelf-life of the fruits and/or a firmer watermelon rind.

Such a reduced function C1MBP 17_2 protein can be obtained by the transcription and translation of a "mutant C1MBP 17_2 allele" which is, for example, a wild-type C1MBP 17_2 allele, which comprises one or more mutations in its nucleic acid sequence. In one aspect, such a mutant C1MBP 17_2 allele is a wild-type C1MBP 17_2 allele, which comprises one or more mutations that preferably result in the production of an C1MBP 17_2 protein wherein at least one conserved and/or functional amino acid is substituted for another amino acid, such that the biological activity is significantly reduced but not completely abolished. However, other mutations, such as one or more non-sense, missense, splice-site or frameshift mutations in the watermelon C1MBP 17_2 allele may also result in reduced function C1MBP 17_2 protein and such reduced function proteins may have one or more amino acids replaced, inserted or deleted, relative to the wild type C1MBP 17_2 protein. Such mutant C1MBP 17_2 allele may also encode a dominant negative C1MBP 17_2 protein, which is capable of adversely affecting the biological activity of other C1MBP 17_2 proteins within the same cell. Such a dominant negative C1MBP 17_2 protein can be an C1MBP 17_2 protein that is still capable of interacting with the same elements as the wild-type C1MBP 17_2 protein, but that blocks some aspect of its function. Examples of dominant negative C1MBP 17_2 proteins are C1MBP 17_2 proteins that lack, or have modifications in specific amino acid residues critical for activation, but still contain their binding domain, such that not only their own biological activity is reduced or abolished, but that they further reduce the total C1MBP 17_2 activity in the cell by competing with wild type and/or partial knockout C1MBP 17_2 proteins present in the cell for binding sites. Mutant alleles are "induced mutant" alleles, which are induced by human intervention, e.g. by mutagenesis. In one aspect the mutant allele is an allele encoding the protein of SEQ ID NO: 1, wherein amino acid number 36 (Serine) is replaced by a different amino acid. In one aspect amino acid number 36 is Phenylalanine (Phe or F). In another aspect amino acid number 36 is replaced by a different amino acid. In another aspect amino acid number 36 is deleted.

A "mutation" in a nucleic acid molecule coding for a protein is a change of one or more nucleotides compared to the wild type sequence, e.g. by replacement, deletion or insertion of one or more nucleotides. Examples of such a mutation are point mutation, nonsense mutation, missense mutation, splice-site mutation, frame shift mutation or a mutation in a regulatory sequence.

A "point mutation" is the replacement of a single nucleotide, or the insertion or deletion of a single nucleotide.

A "nonsense" mutation is a (point) mutation in a nucleic acid sequence encoding a protein, whereby a codon is changed into a stop codon. This results in a premature stop codon being present in the mRNA and in a truncated protein. A truncated protein may have reduced function or loss of function.

A "missense" or non-synonymous mutation is a (point) mutation in a nucleic acid sequence encoding a protein, whereby a codon is changed to code for a different amino acid. The resulting protein may have reduced function or loss of function.

A "splice-site" mutation is a mutation in a nucleic acid sequence encoding a protein, whereby RNA splicing of the pre-mRNA is changed, resulting in an mRNA having a different nucleotide sequence and a protein having a different amino acid sequence than the wild type. The resulting protein may have reduced function or loss of function.

A "frame-shift" mutation is a mutation in a nucleic acid sequence encoding a protein by which the reading frame of the mRNA is changed, resulting in a different amino acid sequence. The resulting protein may have reduced function or loss of function.

A mutation in a regulatory sequence, e.g. in a promoter of a gene, is a change of one or more nucleotides compared to the wild type sequence, e.g. by replacement, deletion or insertion of one or more nucleotides, leading for example to reduced or no mRNA transcript of the gene being made.

A "mutation" in a protein is a change of one or more amino acid residues compared to the wild type sequence, e.g. by replacement, deletion or insertion of one or more amino acid residues. Optionally, a mutation in a protein includes a lower level of wild type protein (e.g. due to a lower expression) in a particular tissue at a specified development stage. Such lower level of protein may be cause by a mutation in a regulatory sequence of the gene encoding the protein.

"Silencing" refers to a down-regulation or complete inhibition of gene expression of the target gene or gene family.

A "target gene" in gene silencing approaches is the gene or gene family (or one or more specific alleles of the gene) of which the endogenous gene expression is down-regulated or completely inhibited (silenced) when a chimeric silencing gene (or 'chimeric RNAi gene') is expressed and for example produces a silencing RNA transcript (e.g. a dsRNA or hairpin RNA capable of silencing the endogenous target gene expression). In mutagenesis approaches, a target gene is the endogenous gene which is to be mutated, leading to a change in (reduction or loss of) gene expression or a change in (reduction or loss of) function of the encoded protein.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous and, where necessary to join two protein encoding regions, contiguous and in reading frame so as to produce a "chimeric protein". A "chimeric protein" or "hybrid protein" is a protein composed of various protein "domains" (or motifs) which is not found as such in nature but which a joined to form a functional protein, which displays the functionality of the joined domains. A chimeric protein may also be a fusion protein of two or more proteins occurring in nature.

The term "food" is any substance consumed to provide nutritional support for the body. It is usually of plant or animal origin, and contains essential nutrients, such as carbohydrates, fats, proteins, vitamins, or minerals. The substance is ingested by an organism and assimilated by the organism's cells in an effort to produce energy, maintain life, or stimulate growth. The term food includes both substance consumed to provide nutritional support for the human and animal body.

The term "heterozygous" refers to a plant or plant cell having dissimilar pairs of alleles of a gene for any hereditary characteristic. The term "homozygous" or in "homozygous form" refers to a plant or plant cell or plant part (e.g. a fruit) having identical alleles of a gene for any hereditary characteristic, e.g. a diploid plant or plant part homozygous for the mutant C1MBP 17_2 allele comprises two copies of the allele in its genome, a triploid plant or plant part comprises three copies and a tetraploid plant or plant part comprises four copies.

The term "shelf life" or "post-harvest shelf life" designates the (average) length of time that a fruit is given before it is considered unsuitable for sale or consumption ('bad'). Shelf life is the period of time that products can be stored, during which the defined quality of a specified proportion of the goods remains acceptable under expected conditions of distribution, storage and display. Shelf life is influenced by several factors: exposure to light and heat, transmission of gases (including humidity), mechanical stresses, and contamination by things such as micro-organisms. Product quality is often mathematically modelled around the fruit firmness/softness parameter. Shelf-life can be defined as the (average) time it takes for fruits of a plant line to start to become bad and unsuitable for sale or consumption, starting for example from harvest. In one embodiment the fruits or fruit parts of plants comprising the mutant alleles according to the invention in homozygous form have a shelf life that is significantly longer than the shelf life of fruits or fruit parts of wild type plants, for example the number of days from harvest of a number of mature fruits (e.g. 2, 4, 6, 8, 10, 12, 14, or 16 or more fruits) up to the first fruit starting to become 'bad' and unsuitable for sale or consumption is significantly longer, e.g. at least 1, 2, 3, 4, 5, 6, 7, 8, 9, 10, or more, days longer than fruits or fruit parts of control plants (such as wild type C1MBP 17_2 plants), when plants are grown under the same conditions and fruits or fruit parts are treated the same way and kept under the same conditions. Thus, to determine the number of days required from a certain stage (e.g. harvest stage) to 'bad' stage, the day when the first fruit of the fruits of the wild type control plant (grown under the same conditions as the mutant plants and being at the same developmental stage) enters a certain stage (e.g. harvest stage) can, for example, be taken as the starting point (day 1) from when on periodically (at certain time intervals, e.g. after 1, 2, 3, 4, 5 or 6 days) the fruits are observed until the day that the first fruit has passed the fully ripe stage and becomes 'bad' (as determinable visually and/or through assessing fruit softness).

In this application the words "improved", "increased", "longer" and "extended" as used in conjunction with the word "shelf-life" are interchangeable and all mean that the fruits or fruit parts of a watermelon plant according to the invention have on average, a longer shelf-life than the control fruits or fruit parts (such as wild type C1MBP 17_2 fruits).

It is understood that comparisons between different plant lines involves growing a number of plants of a line (e.g. at least 5 plants, preferably at least 10 plants per line) under the same conditions as the plants of one or more control plant lines (preferably wild type plants or plants having the same genetics as the line it is compared with except for the C1MBP 17_2 allele, e.g. wild type C1MBP 17_2 plants) and the determination of statistically significant differences between the plant lines or between the fruits or fruit parts of the plant lines when grown under the same environmental conditions and when treated in the same way.

"Juice leakage" (or "leakage" or "liquid leakage") of watermelon fruit flesh can be determined in various ways: e.g by cutting mature watermelon fruits into parts of about 2×2×2 cm or about 3×3×3 cm or about 4×4×4 cm or other sizes. The parts should be free of rind. Juice leakage, i.e. the amount of liquid that leaks from the cut fruit parts, can be determined at different intervals (e.g. 1, 2, 3, 4, 5, 6, 7, and 8 hours after cutting the parts; or 2, 4, 6, 8, 24, 26, 28, 30, and 32 hours after cutting the parts; or 8, 24, 48, and 72 hours after cutting the parts; or 1, 2, 3, 4, 5, 6, 7, 8, 24, 26, 28, 30, 32, 48, 54, 72 hours after cutting the parts).

Percent juice leakage can be determined by weight after each storage interval, using the formula [{(juice weight)}/{fruit parts weight at T=0}]×100% wherein "juice weight" represents the weight of the liquid that comes out of the parts, i.e. leakage; and wherein "fruit parts weight at T=0" is the weight of the fruit parts immediately after cutting the parts. Alternatively, juice leakage can be determined by measuring the amount (in ml) of liquid being released from a given amount of watermelon parts over time. For example by cutting 100, 250, 500 or 1.000 g of watermelon fruit flesh into parts (vide supra) and measuring the amount of leakage at various intervals (vide supra).

It is understood that similar fruit part sizes should be used when comparing different plant lines as the part size affects leakage. Cutting watermelon fruit flesh may damage the fruit flesh leading to increased leakage. It is further understood that during leakage determination, the fruit parts of different plant lines being compared should be stored under equal conditions.

"Stringent hybridization conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridises to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) and Sambrook and Russell (2001).

"Sequence identity" and "sequence similarity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimises the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS, accessible at world wide web under ebi.ac.uk/Tools/emboss/. Alternatively sequence similarity or identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 90%, 95%, 98%, 99% or more (as determined by Emboss "needle" using default parameters, i.e. gap creation penalty=10, gap extension penalty=0.5, using scoring matrix DNAFULL for nucleic acids an Blosum62 for proteins). Such sequences are also referred to as 'variants' herein, e.g. other allelic variants of the C1MBP 17_2 alleles and C1MBP 17_2 proteins than the specific nucleic acid and protein sequences disclosed herein can be identified. Allelic variants may for example exist in other cultivated *Citrullus lanatus* material or in wild *Citrullus lanatus* accessions. Mutations in such allelic variants of the C1MBP 17_2 gene have the same effect on fruit texture of the fruits comprising such variants and cultivated watermelon plants comprising mutations in such variants are embodiments of the invention.

"Wild type allele" (WT) refers herein to a version of a gene encoding a fully functional protein (wild type protein). Such a sequence encoding a fully functional C1MBP 17_2 protein is for example the wild type C1MBP 17_2 cDNA (mRNA) sequence depicted in SEQ ID NO: 2, or the wild type C1MBP 17_2 genomic sequence depicted in SEQ ID NO: 3. The protein sequence encoded by this wild type C1MBP 17_2 mRNA is depicted in SEQ ID NO: 1. It consists of 227 amino acids. Other fully functional C1MBP 17_2 protein encoding alleles (i.e. variant alleles, or allelic variants) may exist in other *Citrullus lanatus* var. *lanatus* plants and may comprise substantial sequence identity with SEQ ID NO: 1, i.e. at least about 90%, 95%, 98%, 99%, 99.2%, 99.3%, 99.4%, 99.5%, 99.6%, 99.7% sequence identity with SEQ ID NO: 1. Such fully functional wild type C1MBP 17_2 proteins are herein referred to as "variants" of SEQ ID NO: 1. Likewise the nucleotide sequences encoding such fully functional C1MBP 17_2 proteins are referred to as variants of SEQ ID NO: 2 and SEQ ID NO: 3.

Thus, cultivated watermelon plants comprising one or more mutations (that lead to one or more amino acids being replaced, inserted and/or deleted) in the endogenous *C. lanatus* var. *lanatus* C1MBP 17_2 allele or variant allele, whereby the presence of the mutant allele in homozygous form leads to a high texture fruit phenotype are part of the invention.

The following mutant C1MBP 17_2 allele is only one exemplary allele of the high texture and/or firm flesh watermelon fruit and/or extended shelf-life conferring C1MBP 17_2 mutation identified according to the present invention. Watermelon plants comprising other mutations in the C1MBP 17_2 allele, which result in a reduced wild type C1MBP 17_2 protein level or a mutant C1MBP 17_2 protein with reduced function or loss-of-function are encompassed and can easily be generated by the skilled person, e.g. by mutagenesis and TILLING. It is noted that nucleotide sequences referred to herein (SEQ ID NO: 2 and SEQ ID NO: 5) are cDNA, i.e. coding DNA sequences, encoding the proteins of SEQ ID NO: 1 and 4, respectively. Obviously, when reference is made to these cDNA nucleotide sequences, it is understood that the cDNA is the coding region of the corresponding *Citrullus lanatus* var. *lanatus* genomic C1MBP 17_2 sequence, which, however, additionally contains introns and therefore the nucleotides have different numbering. Thus, when reference is made to a watermelon plant comprising an C1MBP 17_2 sequence according to e.g. any one of SEQ ID NO: 2 or SEQ ID NO: 5, it is, therefore, understood that the watermelon plant comprising the genomic C1MBP 17_2 sequence which comprises the coding DNA (cDNA), from which the mRNA of SEQ ID NO: 2 or SEQ ID NO: 5 is transcribed (and which is in turn translated into protein). The mRNA has the same nucleotide sequence as the cDNA, except that Thymine (t) is Uracil (u) in the mRNA. Further, when reference is made to a watermelon plant comprising a nucleotide sequence encoding a protein according to the invention (such as a mutant protein of SEQ ID No: 4, or a different mutant), this encompasses different nucleotide sequences, due to the degeneracy of the genetic code. In one embodiment the plant comprises the genomic C1MBP 17_2 sequence depicted in SEQ ID NO:3 or a genomic C1MBP 17_2 sequence substantially identical thereto (e.g. having at least about 70%, 75%, 80%, 85%, 90%, 95%, 98%, 99%, 99.2%, 99.3%, 99.4%, 99.5%, 99.6%, 99.7% sequence identity with SEQ ID NO: 6), but with one or more mutations in said sequence, especially in the exons of said genomic sequence (Exons 1-8 are located from nucleotides form 1002-1191; 5525-5606; 6295-6356; 7184-7295; 7406-7447; 7560-7601; 8726-8883; 9265-9444 of SEQ ID NO:3, respectively causing reduced function or loss of function of the encoded mutant C1MBP 17_2 protein.

The genomic C1MBP 17_2 DNA is depicted in SEQ ID NO: 3. It contains 8 exons interrupted by 7 introns. Exons 1-8 are located from nucleotides 1002-1191; 5525-5606; 6295-6356; 7184-7295; 7406-7447; 7560-7601; 8726-8883; 9265-9444 of SEQ ID NO:3, respectively. The ATG start codon starts at nucleotide 1010 of SEQ ID NO: 3, which corresponds to nucleotide 9 of exon 1.

In one embodiment of the invention (cDNA or genomic) nucleic acid sequences encoding such mutant C1MBP 17_2 proteins comprise one or more non-sense and/or mis-sense mutations, e.g. transitions (replacement of purine with another purine (A⇋G) or pyrimidine with another pyrimidine (C⇋T)) or transversions (replacement of purine with pyrimidine, or vice versa (C/T⇋A/G). In one embodiment the non-sense and/or mis-sense mutation(s) is/are in the nucleotide sequence encoding any of the C1MBP 17_2 exons.

In one embodiment a C1MBP 17_2 nucleotide sequence comprising one or more non-sense and/or mis-sense and/or frame-shift mutations in exon 1 are provided. In another embodiment a C1MBP 17_2 nucleotide sequence comprising one or more non-sense and/or mis-sense and/or frame-shift mutations in the exon 2-, exon 3-, exon 4-, exon 5-, exon 6-, exon 7- and/or exon 8-encoding sequence are provided, as well as a plant comprising such a mutant allele in homozygous form resulting in firmer fruit flesh and/or reduced leakage of watermelon fruit parts and/or longer shelf-life of the fruits and/or a firmer watermelon rind compared to watermelon being homozygous for the wild type C1MBP 17_2 allele.

One exemplary missense mutant C1MBP 17_2 allele (mutant 39) conferring (when in homozygous form) high texture fruit flesh (i.e. firmer fruit flesh and/or reduced leakage of watermelon fruit parts and/or longer shelf-life of the fruits and/or of the fruit parts and/or a firmer watermelon rind) identified according to the present invention, comprises a mutation in exon 1, resulting in a serine (Ser or S) to phenylalanine (Phe or F) substitution at amino acid 36 in the encoded protein (SEQ ID NO: 1), a S36F mutation. See FIG. 1. The protein sequence of mutant 39 is depicted in SEQ ID NO: 4. The amino acid substitution is due to a C to T mutation at nucleotide 107 of SEQ ID NO: 2 counting A in the ATG of the START CODON as nucleotide position 1. The mutant cDNA is depicted in SEQ ID NO: 5.

"Mutant allele" refers herein to an allele comprising one or more mutations in the coding sequence (mRNA, cDNA or genomic sequence) compared to the wild type allele. Such mutation(s) (e.g. insertion, inversion, deletion and/or replacement of one or more nucleotide(s)) may lead to the encoded protein having reduced in vitro and/or in vivo functionality (reduced function) or no in vitro and/or in vivo functionality (loss-of-function), e.g. due to the protein e.g. being truncated or having an amino acid sequence wherein one or more amino acids are deleted, inserted or replaced. Such changes may lead to the protein having a different 3D conformation, being targeted to a different sub-cellular compartment, having a modified catalytic domain, having a modified binding activity to nucleic acids or proteins, etc. In certain aspects "mutant allele" also refers to a mutation in the endogenous regulatory sequence(s) of a gene, such as the promoter region, whereby expression of the wild type mRNA is reduced or even abolished. For example, embodiments wherein the C1MBP 17_2 wild type protein levels are significantly reduced (or even abolished) in order to generate plants with a high texture fruit phenotype comprise one or more mutations in regulatory sequences of the C1MBP 17_2 gene resulting in significantly reduced (or abolished) gene expression.

"Wild type plant" and "wild type fruits" or "normal" plants/fruits refers herein to a watermelon plant comprising two copies of a wild type (WT) C1MBP 17_2 allele (C1MBP 17_2/C1MBP 17_2) encoding a fully functional C1MBP 17_2 protein (e.g. in contrast to "mutant plants", comprising a mutant C1MBP 17_2 allele). Such plants are for example suitable controls in phenotypic assays. Preferably wild type and/or mutant plants are "cultivated watermelon plants". For example the Nunhems' varieties Montreal, Freedom, Revolution, Premium, Crispy Red, Pixie, or Selecta; or cultivar All Sweet, or Charleston Gray, or Crimson Sweet, or Jubilee and many others.

"Watermelon plants" or "cultivated watermelon plants" are plants of the *Citrullus lanatus* var. *lanatus*, i.e. varieties, breeding lines or cultivars of the species *Citrullus lanatus* var. *lanatus*, cultivated by humans and having good agronomic characteristics; preferably such plants are not "wild plants", i.e. plants which generally have much poorer yields and poorer agronomic characteristics than cultivated plants (e.g. brix of ripe fruits below 5). "Wild plants" include for example *Citrullus lanatus* var. *citroides*.

"Brix" or "degree Brix" or "° brix" refers to the mean total soluble solids content as measured on several mature fruits using a refractometer. Preferably the mean of at least three fruits, each measured between the centre and the rind of the cut-open fruit, is calculated. Alternatively fruit flesh or slices can be homogenized as described in the examples and the brix can be measured.

It is understood that fruit and plant characteristics are preferably determined on more than one fruit or plant e.g. at least 2, 3, 4, 5, 10, 15, or even at least 20. When determined on multiple fruits or plants, an average value can be determined using methods known in the art (arithmetic mean).

"Uniform fruit flesh color" means that the color throughout the mature fruits, when cut open through the middle (midsection), is evenly distributed throughout the fruit flesh, i.e. not patchy. Thus, a red fruit is red throughout the fruit flesh and does not contain white patches. An example of a fruit with uniform red color is the diploid variety Premium F1 (Nunhems).

Preferably, the mutant plants also have good other agronomic characteristics, i.e. they do not have reduced fruit numbers and/or reduced fruit quality compared to wild type plants. In a preferred embodiment the plant is a watermelon plant and the fruit is a watermelon fruit. Thus, also harvested products of plants or plant parts comprising one or more (two, three or four) mutant C1MBP 17_2 alleles are provided. This includes downstream processed products, such as canned fruit, dried fruit, peeled fruit, etc. The products can be identified by comprising the mutant allele in their genomic DNA.

FIGURES

FIG. 1 shows a pairwise alignment between the wild type C1MBP 17_2 protein of wild type plants (comprising normal fruits) represented by SEQ ID NO: 1, and the mutant C1MBP 17_2 protein of mutant plant 39, having high texture fruits, and represented by SEQ ID NO: 4.

FIG. 2 shows a transversally cut in halves watermelon fruit showing data collection points M1-M4 for the fruit firmness measurement. The first location M1 is in the center (central column) of the fruit and the other three measurement points (2, 3, 4) are on the interlocular tissue at about two-third of the radius from the center to the rind, just outside the drawn circle. The ticket indicating 1436 refers to an internal plant reference number.

FIG. 3 designation of outer and inner fruit flesh cubes from a slice of a watermelon fruit in the juice leakage protocol.

BRIEF DESCRIPTION OF THE SEQUENCE LISTING

Figure 2:
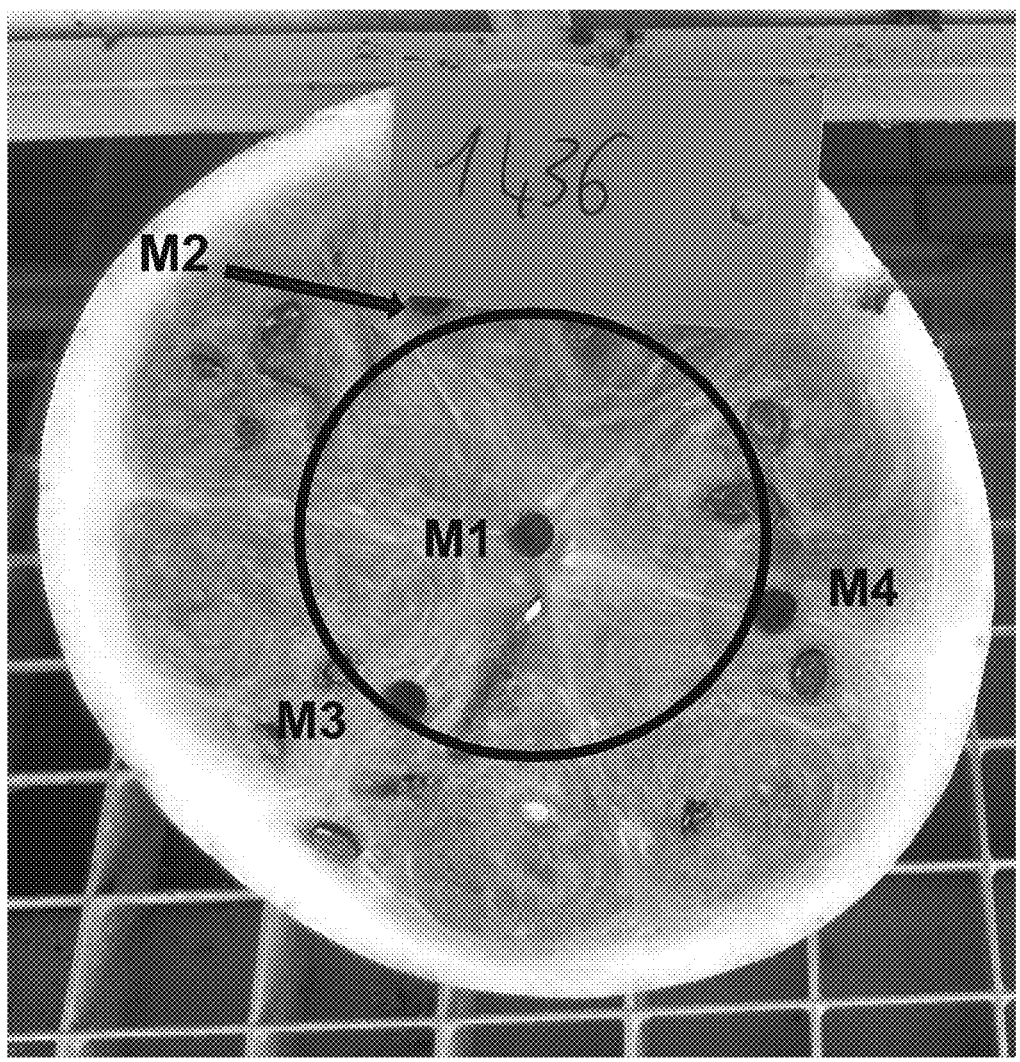

SEQ ID NO: 1 shows the *Citrullus lanatus* var. *lanatus* wild type, fully functional, C1MBP 17_2 protein sequence.

SEQ ID NO: 2 shows the corresponding *Citrullus lanatus* var. *lanatus* wild type C1MBP 17_2 cDNA (mRNA) sequence.

SEQ ID NO: 3 shows the *Citrullus lanatus* var. *lanatus* wild type C1MBP 17_2 genomic DNA sequence.

SEQ ID NO: 4 shows the *Citrullus lanatus* var. *lanatus* mutant 39 C1MBP 17_2 protein sequence.

SEQ ID NO: 5 shows the *Citrullus lanatus* var. *lanatus* mutant 39 C1MBP 17_2 (cDNA) mRNA sequence.

SEQ ID NO: 6 shows the *Citrullus lanatus* var. *lanatus* mutant 39 C1MBP 17_2 genomic DNA sequence.

DETAILED DESCRIPTION OF THE INVENTION

The present invention discloses a plant of the species *Citrullus lanatus* var. *lanatus* (i.e. a cultivated watermelon) wherein i) the plant comprises one or more mutations in the C1MBP 17_2 allele and ii) wherein said allele encodes a mutant protein comprising one or more amino acids mutations (i.e. replaced, inserted and/or deleted) relative to the wild type C1MBP 17_2 protein of SEQ ID NO: 1. Such a plant differs from the prior art in that the C1MBP 17_2 allele is located on chromosome 8 while other firm flesh watermelon plants have a firm flesh QTL locus located on chromosome 9 or 6 (US2013/055466), which QTL is an introgression from a South African accession, PI296341, of *C. lanatus* var. *citroides* (EP2443919). Thus, the plants of the invention comprise a genome of cultivated watermelon, comprising a mutant C1MBP 17_2 allele on (cultivated watermelon) chromosome 8, while the prior art describes watermelon plants comprising an introgression of a wild accession, i.e. having a recombinant chromosome 9 or 6 comprising a wild introgression fragment.

In another embodiment the plant of the invention comprising one or more mutations in the C1MBP 17_2 allele and comprising the allele in homozygous form produces fruits/is capable of producing fruits with high texture fruit flesh.

In one aspect, the plant comprises a mutant C1MBP 17_2 allele, wherein an amino acid in exon 1 (amino acids 1 to 60 of SEQ ID NO: 1), especially in the MADS domain of exon 1 (amino acids 2 to 58), preferably amino acid number 36, of the wild type C1MBP 17_2 protein of SEQ ID NO: 1 is replaced by a different amino acid. In one aspect amino acid number 36 of SEQ ID NO: 1 is a Phenylalanine (Phe or F) instead of Serine (Ser or S). Amino acids 2 to 58 comprise a putative MADS-domain.

In one embodiment the invention discloses a plant of the species *Citrullus lanatus* var. *lanatus* wherein i) the plant comprises one or more mutations in the C1MBP 17_2 allele and ii) wherein said allele encodes a mutant protein comprising one or more amino acid mutations (i.e. replaced, inserted and/or deleted) relative to the wild type C1MBP 17_2 protein of SEQ ID NO: 1, and optionally iii) wherein said one or more mutated (i.e. replaced, inserted and or deleted) amino acids result in a protein of reduced function or no function compared to wild type plants.

In another embodiment, the plant of the invention, i.e. a plant of the species *Citrullus lanatus* var. *lanatus* wherein i)

the plant comprises one or more mutations in the C1MBP 17_2 allele and ii) wherein said allele encodes a mutant protein comprising one or more amino acid mutations (i.e. replaced, inserted and/or deleted) relative to the wild type C1MBP 17_2 protein of SEQ ID NO: 1, and optionally iii) wherein said plant does not comprise an introgression which affects fruit firmness and/or juice leakage from a South African accession, PI296341, of *C. lanatus* var. *citroides* (such as disclosed in EP2443919).

In a further embodiment, the plant of the invention, i.e. a plant of the species *Citrullus lanatus* var. *lanatus* wherein i) the plant comprises one or more mutations in the C1MBP 17_2 allele and ii) wherein said allele encodes a mutant protein comprising one or more amino acids mutations (i.e. replaced, inserted and/or deleted) relative to the wild type C1MBP 17_2 protein of SEQ ID NO: 1, and optionally iii) wherein said plant does not comprise an introgression which affects fruit firmness and/or juice leakage from a wild plant such as of *C. lanatus* var. *citroides*.

A further embodiment the invention discloses a plant of the species *Citrullus lanatus* var. *lanatus* wherein i) the plant comprises a reduced level of wild type C1MBP 17_2 protein of SEQ ID NO: 1, wherein said reduced level is due to a reduction in gene expression of the endogenous wild type C1MBP 17_2 gene or wherein the reduced level is due to one or more mutations in the coding sequence of the C1MBP 17_2 gene resulting in one or more amino acids being replaced, inserted and/or deleted relative to the wild type C1MBP 17_2 protein of SEQ ID NO: 1. Thus, either the regulatory region(s) of the C1MBP 17_2 gene are mutated, leading to a reduced gene expression (or no gene expression) of the wild type gene and/or the coding sequence comprises one or more mutations leading to the expression of a C1MBP 17_2 protein comprising one or more amino acid insertions, deletions and/or replacements relative to the wild type protein, whereby the protein function is reduced or abolished. When two copies of such mutant C1MBP 17_2 genes are present in the plant (i.e. when the levels of the functional wild type C1MBP 17_2 protein are significantly reduced or absent), the fruit flesh has a high texture.

Any other fruit characteristics may be combined with the high texture fruit flesh by breeding. As mentioned, for example fruit shape (e.g. elongate, oval, blocky, spherical or round), fruit surface (furrow, smooth), flesh color (scarlet red, coral red, orange, salmon, yellow, canary yellow or white), rind color (e.g. light green; dark green; green-striped with narrow, medium or wide stripes; grey types; with or without spotting; Golden yellow), rind thickness, rind toughness, rind pattern (e.g. striped, non-striped, netted), brix (total soluble solids), flesh structure, higher lycopene and/or vitamin content, different sugar:acid ratios, very good fruit flavour, etc. may be modified by breeding. See Guner and Wehner 2004, Hort Science 39(6): 1175-1182, in particular pages 1180-1181 describing genes for fruit characteristics. Generally important breeding objectives are early maturity, high fruit yield, high internal fruit quality (good uniform color, high sugar, proper sugar:acid ratio, good flavor, high vitamin and lycopene content, firm flesh texture, non-fibrous flesh texture, freedom from defects such as hollow heart, rind necrosis, blossom-end rot or cross stitch and good rind characteristics and cracking-resistance).

In one embodiment of the invention, the fruits preferably also do not have a "brittle rind" and/or an "explosive rind" as described in WO03/075641 on page 13 and 14, i.e. the fruits do not break under pressure in the range of 90 to 140 g/mm$^2$.

In another embodiment the invention relates to a plant of the species *Citrullus lanatus* var *lanatus* wherein i) the plant comprises one or more mutations in the C1MBP 17_2 allele and ii) wherein said allele encodes a mutant protein comprising one or more amino acids mutations (i.e. replaced, inserted and/or deleted) relative to the wild type C1MBP 17_2 protein of SEQ ID NO: 1, and iii) wherein said one or more mutated (i.e. replaced, inserted and or deleted) amino acids result in a protein of reduced function or no function; compared to a control plants lacking the allele encoding said mutant protein.

In yet another embodiment the control plant comprises two copies of the allele encoding the wild type/fully functional protein, which is also normally expressed. Suitable control plants are thus currently available watermelon varieties, having wild type alleles of the C1MBP 17_2 gene. In still another embodiment the control plant is genetically the same as the plant of the invention, except for the one or more mutations in the C1MBP 17_2 allele.

In one aspect the plant of the invention comprising one or more mutations in the C1MBP 17_2 allele is a cultivated watermelon plant.

In another aspect the plant of the invention comprising one or more mutations in the C1MBP 17_2 allele results in lower levels of wild type mRNA levels and lower levels of wild type C1MBP 17_2 protein levels in the plant, especially in the fruits. mRNA and protein levels can be determined in mature fruits or unripe fruits, using methods known in the art. In one aspect the wild type C1MBP 17_2 mRNA or protein level in mature fruits are at least 2%, or at least 5%, e.g. at least 10%, 12%, 14%, 16%, 18% or 20% lower than in fruits of control plants. In another embodiment the wild type C1MBP 17_2 mRNA or protein level in unripe fruits are at least 2%, or at least 5%, e.g. at least 10%, 12%, 14%, 16%, 18% or 20% lower than in fruits of control plants.

In one aspect the one or more mutations in the C1MBP 17_2 allele encoding the mutant C1MBP 17_2 protein, whereby the mutant protein comprises 1 or 2 or 3 or 4 or 5 or 6 or 7 or 8 or 9 or 10 mutations. In another embodiments the one or more mutations in the C1MBP 17_2 allele encoding the mutant C1MBP 17_2 protein, whereby the mutant protein comprises 1 or 2 or 3 or 4 or 5 or 6 or 7 or 8 or 9 or 10 amino acid substitutions compared to the wild type protein.

In one aspect the plant of the invention comprising two copies of a mutant C1MBP 17_2 allele of the invention (resulting in reduced levels of wild type C1MBP 17_2 protein or production of reduced-function or loss of function C1MBP 17_2 protein) produces (is capable of producing) fruits having high texture fruit flesh.

In another embodiment the plant of the invention comprising one or more mutations in the C1MBP 17_2 allele produces a mutant C1MBP 17_2 protein comprising one or more amino acids replaced, inserted and/or deleted relative to the wild type C1MBP 17_2 protein, wherein the (functional) wild type C1MBP 17_2 protein comprises at least 85% amino acid sequence identity with SEQ ID NO: 1, e.g. having at least 90%, 91%, 92%, 93%, 94%, 95%, 96%, 97%, 98%, 99%, or even at least 99.2%, 99.4%, 99.6%, 99.8% or at least 99.9% amino acid sequence identity with SEQ ID NO: 1. Thus, mutations which result in reduced function or loss-of-function of the C1MBP 17_2 protein can also be introduced into functional variants of the C1MBP 17_2 gene.

In another embodiment the plant of the invention comprising one or more mutations in the C1MBP 17_2 allele produces a mutant C1MBP 17_2 protein comprising a Serine 36 to Phenylalanine (S36F) substitution in SEQ ID NO: 1, or in variants thereof, said variants having at least 85% amino acid sequence identity with SEQ ID NO: 1 and having said S36F amino acid substitution or the equivalent amino acid position in a variant C1MBP 17_2 protein. In one aspect such variants have at least 86% amino acid sequence identity with SEQ ID NO: 1, e.g. have at least 90%, 91%, 92%, 93%, 94%, 95%, 96%, 97%, 98%, 99%, or even at least 99.1%, 99.2%, 99.3%, 99.4%, 99.5% or 99.6% amino acid sequence identity with SEQ ID NO: 1.

In yet another embodiment the plant of the invention comprising one or more mutations in the C1MBP 17_2 allele is a cultivated watermelon plant, or a part thereof, such as a fruit produced on the plant.

In another embodiment the plant of the invention comprising one or more mutations in the C1MBP 17_2 allele is an inbred watermelon line or a hybrid watermelon, or a part thereof, such as a fruit produced on the plant.

In yet another embodiment the plant of the invention comprising one or more mutations in the C1MBP 17_2 allele is a diploid watermelon plant, e.g. a pollenizer plant, or a part thereof, such as a fruit produced on the plant, or pollen.

In yet another embodiment the plant of the invention comprising one or more mutations in the C1MBP 17_2 allele is a triploid watermelon plant, or a part thereof, such as a seedless, triploid fruit produced on the plant.

In yet another embodiment the plant of the invention comprising one or more mutations in the C1MBP 17_2 allele is a tetraploid watermelon plant, or a part thereof, such as a fruit produced on the plant.

In yet another embodiment the plant of the invention comprising one or more mutations in the C1MBP 17_2 allele is a F1 hybrid plant, or a part thereof, such as a fruit produced on the plant.

The plants and plant parts may comprise the mutant allele in heterozygous form or in homozygous form. As the mutant allele is "homozygous recessive", it is preferred that the plants only comprise the mutant allele, i.e. a diploid plant or plant part comprises two copies, a tetraploid plant or plant part comprises four copies, a triploid plant or plant part comprises three copies of the mutant allele in its genome (and they lack the dominant wild type allele). Tetraploids are produced by duplication the genome of a diploid plant, which comprises two copies of the mutant allele (homozygous). Seeds of triploid plants are produced by crossing a diploid parent (comprising two copies of the mutant allele) with a tetraploid parent (comprising four copies of the mutant allele). The triploid seeds can be sown and a diploid, wild type pollenizer can be used to initiate fruit formation. Fruits are seedless and comprise three copies of the mutant allele.

In still another embodiment the plant of the invention comprising one or more mutations in the C1MBP 17_2 allele and comprising the allele in homozygous form (i.e. two copies in a diploid plant, three copies in a triploid plant and four copies in a tetraploid plant) produces mature fruits having an average fruit flesh firmness at the center (central column) of transversally cut-in-halves fruits of at least 3.50 kg, preferably at least 3.75, 4.0, 4.2, 4.4, 4.5, 4.6, 4.8, 5.0, 5.2, 5.4, 5.6, 5.7, 5.8, 5.9, 6.0, or even at least 6.1 kg when a tip of 9 mm diameter is inserted into the flesh to a depth of 20 mm. Preferably the measurements are overall averages of several plants of a line or variety (e.g. at least 3 plants) and several fruits (e.g. at least three fruits) of the plants.

It is understood that fruit flesh firmness expressed in kilogram (kg) can be converted into $kg/cm^2$. As in this case a tip with a diameter of 9.0 mm was used, the firmness value in kg should be divided by 0.64 (tip surface being $0.64\ cm^2$). Likewise the $kg/cm^2$ value can be multiplied by 9.80665 to convert it to $N/cm^2$ (i.e. kilogram to Newton conversion).

So in one embodiment the invention provides a plant of the invention comprising one or more mutations in the C1MBP 17_2 allele and comprising the allele in homozygous form (i.e. two copies in a diploid plant, three copies in a triploid plant and four copies in a tetraploid plant) producing mature fruits having an average fruit flesh firmness at the center (central column) of transversally cut-in-halves fruits of at least 5.47 $kg/cm^2$, preferably at least 5.86, 6.25, 6.56, 6.88, 7.03, 7.19, 7.50, 7.81, 8.13, 8.44, 8.75, 8.91, 9.06, 9.22, or even at least 9.38 $kg/cm^2$ when a tip of 9 mm diameter is inserted into the flesh to a depth of 20 mm.

In another embodiment the invention provides a plant comprising one or more mutations in the C1MBP 17_2 allele and comprising the allele in homozygous form (i.e. two copies in a diploid plant, three copies in a triploid plant and four copies in a tetraploid plant) producing mature fruits having an average fruit flesh firmness at the center (central column) of transversally cut-in-halves fruits of at least 53.63 $N/cm^2$, preferably at least 57.46, 61.29, 64.36, 67.42, 68.95, 70.49, 73.55, 76.61, 79.68, 82.74, 85.81, 87.34, 88.87, 90.41, 91.94, or even at least 93.47 $N/cm^2$ when a tip of 9.0 mm diameter is inserted into the flesh to a depth of 20 mm.

In one aspect the plant of the invention comprising one or more mutations in the C1MBP 17_2 allele and comprising the allele in homozygous form (i.e. two copies in a diploid plant, three copies in a triploid plant and four copies in a tetraploid plant) produces mature fruits having an average fruit flesh firmness at the interlocular tissue of transversally cut-in-halves fruits of at least 2.0 kg, preferably at least 2.1, 2.2, 2.3, 2.4, 2.5, 2.6, 2.7, 2.8, 2.9 or even at least 3.0 kg when a tip of 9 mm diameter is inserted into the flesh to a depth of 20 mm. Preferably the measurements are overall averages of several plants of a line or variety (e.g. at least three plants), several fruits of the plants (e.g. at least three fruits) and several interlocular locations per fruit (e.g. at least two locations, preferably at least three locations). It is understood that fruit flesh firmness at the interlocular tissue is measured at about two-third of the radius from the center to the rind.

In another aspect the plant of the invention comprising one or more mutations in the C1MBP 17_2 allele and comprising the allele in homozygous form (i.e. two copies in a diploid plant, three copies in a triploid plant and four copies in a tetraploid plant) produces mature fruits having an average fruit flesh firmness of the interlocular tissue of transversally cut-in-halves fruits of at least 3.13 $kg/cm^2$, preferably at least 3.44, 3.59, 3.75, 3.91, 4.06, 4.22, 4.38, 4.53 $kg/cm^2$, or even at least 4.69 $kg/cm^2$.

In yet another aspect the plant of the invention comprising one or more mutations in the C1MBP 17_2 allele and comprising the allele in homozygous form (i.e. two copies in a diploid plant, three copies in a triploid plant and four copies in a tetraploid plant) produces mature fruits having an average fruit flesh firmness of the interlocular tissue of transversally cut-in-halves fruits of at least 30.65 $N/cm^2$, preferably at least 33.71, 35.24, 36.77, 38.31, 39.84, 41.37, 42.90, 44.44 $N/cm^2$ or even at least 45.97 $N/cm^2$.

The C1MBP 17_2 allele can be present in homozygous or heterozygous form. So in one aspect the plant of the invention comprising one or more mutations in the C1MBP 17_2 allele is homozygous for this mutant allele. In another aspect, the plant is heterozygous for this allele. In yet another aspect, the plant comprises 2 copies of such mutant allele. In still another aspect, the plant comprises 3 copies of such mutant C1MBP 17_2 allele. It is understood that a plant comprising 2 or more mutant C1MBP 17_2 alleles may comprise 2 or more identical; or, 2 or more mutant C1MBP 17_2 alleles that are different to each other.

In one embodiment the plant of the invention comprising one or more mutations in the C1MBP 17_2 and comprising the allele in homozygous form (i.e. two copies in a diploid plant, three copies in a triploid plant and four copies in a tetraploid plant) allele produces mature fruits having an average fruit flesh firmness at the center (central column) of transversally cut-in-halves fruits that is at least 50%, preferably at least 70%, 80%, 90%, 100%, 110%, 120%, 130%, 140%, 150%, 160%, 170%, 180%, 190%, 200%, 210%, 220%, 230%, 240% or even at least 250% higher than the average fruit flesh firmness of fruits of wild type plants (comprising functional copies of the wild type C1MBP 17_2 allele).

In another embodiment the plant of the invention comprising one or more mutations in the C1MBP 17_2 allele and comprising the allele in homozygous form (i.e. two copies in a diploid plant, three copies in a triploid plant and four copies in a tetraploid plant) produces mature fruits having an average fruit flesh firmness at the center (central column) of transversally cut-in-halves fruits that is at least 50%, preferably at least 70%, 80%, 90%, 100%, 110%, 120%, 130%, 140%, or even at least 150%, higher than the average fruit flesh firmness of fruits of control plants lacking the allele encoding said mutant protein; or in another embodiment at least 160%, 170%, 180%, 190%, 200%, 210%, 220%, 230%, 240% or even at least 250% higher than the average fruit flesh firmness of fruits of control plants lacking the allele encoding said mutant protein. In yet another embodiment the control plant only comprises an allele encoding the wild type/fully functional protein. In still another embodiment the control plant is genetically the same as the plant of the invention, except for the one or more mutations in the C1MBP 17_2 allele.

In one aspect he plant of the invention comprising one or more mutations in the C1MBP 17_2 allele and comprising the allele in homozygous form (i.e. two copies in a diploid plant, three copies in a triploid plant and four copies in a tetraploid plant) produces mature fruits having an average fruit flesh firmness measured between the fruit center and rind (interlocular tissue) that is at least 30%, preferably at least 35%, 40%, 41%, 42%, 43%, 44%, 45%, 46% 47%, 48%, 49% or 50% higher than fruits of control plants lacking the allele encoding the mutant C1MBP 17_2 protein. In yet another embodiment the control plant only comprises an allele encoding the wild type/fully functional protein. In still another embodiment the control plant is genetically the same as the plant of the invention, except for the one or more mutations in the C1MBP 17_2 allele. Preferably, fruit flesh firmness measured between the fruit center and rind, should be measured at about half-way between the fruit center and the rind, or more preferably at about ⅓ from the rind to the fruit center.

In another embodiment the plant of the invention comprising one or more mutations in the C1MBP 17_2 allele comprises a nucleic acid sequence encoding a protein according to SEQ ID NO: 1 having one or more amino acid replaced, deleted or inserted. In one aspect one or more amino acids are replaced, especially in one aspect one or more amino acids in exon 1 (amino acids 1 to 60) are replaced, preferably one or more amino acids in the MADS domain (amino acid 2 to 58) are replaced. In one aspect the protein comprises a serine (Ser or S) to phenylalanine (Phe or F) substitution at amino acid 36 of SEQ ID NO: 1 or of a C1MBP 17_2 protein comprising at least 90%, 95%, 96%, 97%, 98% or 99% amino acid sequence identity to SEQ ID NO: 1.

In another embodiment the plant of the invention comprising one or more mutations in the C1MBP 17_2 allele comprises a nucleic acid sequence encoding an mRNA according to SEQ ID NO: 2 having a cytosine substituted for a thymine at position 107 (C107T) or in variants of SEQ ID NO: 2 having at least 70% nucleic acid sequence identity to SEQ ID NO: 2 and having the C107T substitution or the equivalent nucleic acid position in a variant of SEQ ID NO; 2. In one aspect such variant of SEQ ID NO: 2 has at least 75%, 80%, 85% 90% nucleic acid sequence identity with SEQ ID NO: 2, e.g. at least 92%, 94%, 96%, 98%, 99% or even at least 99.2%, 99.4%, 99.6%, 99.8% or even 99.9% nucleic acid sequence identity with SEQ ID NO: 2.

In still another embodiment the plant of the invention comprising one or more mutations in the C1MBP 17_2 allele comprises a genomic a genomic C1MBP 17_2 sequence having at least 70%, (e.g. at least 75%, 80%, 85%, 90%, 95%, 98%, 99%, 99.2%, 99.3%, 99.4%, 99.5%, 99.6%, 99.7%) nucleic acid sequence identity with SEQ ID NO: 3 and encoding a mutant C1MBP 17_2 protein having a Serine 36 to Phenylalanine (S36F) substitution in SEQ ID NO: 1 or in variants thereof, said variants having at least 85% amino acid sequence identity with SEQ ID NO: 1 (e.g. at least 90% or even at least 95%, 96%, 97%, 98% or even at least 99% amino acid sequence identity with SEQ ID NO: 1) and having said S36F amino acid substitution or the equivalent amino acid position.

In one embodiment the genomic C1MBP 17_2 sequence has at least 90% nucleic acid sequence identity with SEQ ID NO: 3 and the variant mutant C1MBP 17_2 protein having a Serine 36 to Phenylalanine (S36F) substitution in SEQ ID NO: 1 or the equivalent amino acid position has at least 90% or even at least 95%, 96%, 97%, 98% or even at least 99% amino acid sequence identity with SEQ ID NO: 1.

In another embodiment the genomic C1MBP 17_2 sequence has at least 98% nucleic acid sequence indent with SEQ ID NO: 3 and the variant mutant C1MBP 17_2 protein having a Serine 36 to Phenylalanine (S36F) substitution in SEQ ID NO: 1 or the equivalent amino acid position has at least 90% or even at least 95%, 96%, 97%, 98% or even at least 99% amino acid sequence identity with SEQ ID NO: 1.

In still another embodiment the plant of the invention comprising one or more mutations in the C1MBP 17_2 allele comprises the C1MBP 17_2 allele as found in, and which is derivable from or obtainable from (or derived from or obtained from) seed deposited under Accession No. NCIMB 42340. The allele can be transferred to other watermelon plants by crossing plants grown from the deposited seeds with another watermelon plant, preferably with another diploid, cultivated watermelon plant.

In yet another aspect, the invention relates a watermelon plant comprising a mutant C1MBP 17_2 allele seeds of which having been deposited under NCIMB Accession No: 42340. In another aspect plants grown from seeds of mutant 39 are capable of producing fruits with high texture fruit flesh (i.e. firmer fruit flesh and/or reduced leakage of watermelon fruit parts and/or longer shelf-life of the fruits and/or a firmer watermelon rind). In yet another aspect, the invention relates to a breeding method comprising the step of obtaining a watermelon plant comprising a mutant C1MBP 17_2 allele, and crossing this plant with another watermelon plant, and optionally selecting progeny comprising the mutant C1MBP 17_2 allele. In another embodiment, the plant comprising the mutant C1MBP 17_2 allele, comprises the C1MBP 17_2 allele as found in, and which is derivable from or obtainable from (or can be derived from or obtained from) seed deposited under Accession No. NCIMB 42340, e.g. by crossing plants grown from NCIMB 42340 with another cultivated watermelon plant. In still another embodiment, the plant comprising the mutant C1MBP 17_2 allele is mutant 39. In another embodiment, the invention relates to a plant obtained via this method.

In another aspect, the invention relates to seeds from which plants of the invention can be grown, i.e. seeds that when sown, grow into a plant of the invention comprising one or more mutations in the C1MBP 17_2 allele.

In a specific embodiment of the invention watermelon plants and plant parts (fruits, seeds, etc.) comprising a C1MBP 17_2 allele comprising one or more mutations are provided. In one aspect, a watermelon fruit of a plant of the invention is provided. In one aspect the fruit is a diploid fruit. In another aspect the fruit is a triploid (seedless) watermelon fruit. In another aspect, the plant part is a plant cell, tissue or part of the seed or fruit of the plant of the invention. In yet another aspect the plant parts are fruit, seeds, pollen, scions, cells or progeny of the plant of the invention comprising the mutant C1MBP 17_2 allele or the mutant C1MBP 17_2 protein.

In yet another aspect, the invention relates to a plant cell, or plant tissue or plant part of the plant of the invention (i.e. comprising a mutation in the C1MBP 17_2 allele). In still another aspect, the invention relates to a plant cell, or plant tissue or part of a seed or fruit from a plant of the invention comprising a mutant C1MBP 17_2 allele.

The invention also relates to food and/or food products incorporating the fruit or part of a fruit of a watermelon plant of the invention. As used herein, food refers to nutrients consumed by human or animal species. It is understood that the C1MBP 17_2 allele comprising one or more mutations as in the plants of the invention, should still be identifiable in this food or food product. In another aspect, the invention relates to a container comprising watermelon fruits of a plant of the invention. In still another aspect, the invention relates to a container comprising parts of watermelon fruits, in particular parts of watermelon fruit flesh of fruits of plants of the invention.

The invention also provides in one aspect a method of producing and/or identifying a *Citrullus lanatus* var *lanatus* (watermelon) plant or plant part (e.g. a fruit or cell) of the invention comprising a step of screening the plant or plant part for the presence in its genome of a C1MBP 17_2 allele encoding a mutant C1MBP 17_2 protein according to the invention. The skilled person knows how to screen for such alleles, using known methods. He can generate PCR primers based on the sequences provided herein and amplify the mRNA (cDNA) or genomic DNA of C1MBP 17_2 and/or sequence the genomic DNA, mRNA or cDNA. He can for example detect the C to T substitution at position 107, of SEQ ID NO: 2 or nucleotide 1116 of SEQ ID NO: 3 to determine whether a mutant allele comprising the S36F mutation is present. In yet another aspect, the invention relates to plants obtained with such method.

In yet another aspect, the invention provides a method of producing *Citrullus lanatus* var *lanatus* plants comprising the steps of
i. providing a *Citrullus lanatus* var *lanatus* plant comprising a mutant C1MBP 17_2 allele as described, e.g. as found in seeds deposited under accession number NCIMB 42340
ii. crossing said *Citrullus lanatus* var *lanatus* plant with a second *Citrullus lanatus* var *lanatus* plant; and
iii. optionally selecting progeny plants.

In one aspect, the progeny plants in step iii. comprise the mutant C1MBP 17_2 allele as found in seeds deposited under accession number NCIMB 42430. In yet another aspect, the invention relates to plants obtained with such method.

In yet another aspect, the invention provides a method of producing *Citrullus lanatus* var *lanatus* plants comprising the steps of:
a. obtaining a first *Citrullus lanatus* var *lanatus* plant of the invention comprising one or more mutations in the C1MBP 17_2 allele encoding a mutant C1MBP 17_2 protein;
b. crossing said first *Citrullus lanatus* var *lanatus* plant with a second *Citrullus lanatus* plant to obtain seeds;
wherein the *Citrullus lanatus* var *lanatus* plant grown from the seeds of step (b) comprises one or more mutations in the C1MBP 17_2 allele encoding a mutant C1MBP 17_2 protein. In another embodiment, in step (b) hybrid seeds are produced. When planted, such hybrid seeds grow into hybrid *Citrullus lanatus* var *lanatus* plants. In one aspect the mutant allele of a. comprises one or more amino acids inserted, replaced or deleted in the MADS domain (amino acids 2 to 58 of SEQ ID NO: 1). In a specific aspect the mutant allele of a. comprises one or more amino acids of amino acid 2 to 58 of SEQ ID NO: 1 replaced by a different amino acid. Plants comprising such mutant C1MBP 17_2 alleles can be generated by mutagenesis, and identified by methods known in the art, e.g. by TILLING. In one aspect the plant under a. comprises the mutant allele in homozygous form. In yet another aspect, the invention relates to plants obtained with such method.

In yet another aspect, the invention provides a method of producing *Citrullus lanatus* var *lanatus* plants comprising the steps of:
a. obtaining a first *Citrullus lanatus* var *lanatus* plant of the invention comprising one or more mutations in the C1MBP 17_2 allele encoding a mutant C1MBP 17_2 protein having a Serine 36 to Phenylalanine (S36F) substitution in SEQ ID NO: 1 or in variants of SEQ ID NO: 1, said variants having at least 85% amino acid sequence identity with SEQ ID NO: 1 and having said S36F amino acid substitution or the equivalent amino acid position in a variant C1MBP 17_2 protein;
b. crossing said first *Citrullus lanatus* var *lanatus* plant with a second *Citrullus lanatus* var *lanatus* plant to obtain seeds; wherein the *Citrullus lanatus* var *lanatus* plant grown from the seeds of step (b) comprises one or more mutations in the C1MBP 17_2 allele encoding a mutant C1MBP 17_2 protein having a Serine 36 to Phenylalanine (S36F) substitution in SEQ ID NO: 1 or in variants of SEQ ID NO: 1, said variants having at least 85% amino acid sequence identity with SEQ ID NO: 1 and having said S36F amino acid substitution. In another embodiment, in step (b) hybrid seeds are produced. When planted, such hybrid seeds grow into hybrid *Citrullus lanatus* var *lanatus* plants. In yet another aspect, the invention relates to plants obtained with such method.

It is understood that when referred to watermelon (*Citrullus lanatus* var *lanatus*) plants capable of producing fruits with high texture fruit phenotype, such watermelon plants will, when grown under normal growing conditions, produce fruits, said fruits will have the high texture fruit phenotype as defined elsewhere in this document.

Further, throughout this document, watermelon plant and *Citrullus lanatus* var *lanatus* (plant) are used interchangeably.

In yet another aspect, the invention provides a *Citrullus lanatus* var *lanatus* plant comprising a mutant C1MBP 17_2 allele wherein the mutant C1MBP 17_2 allele is the allele as present in seeds deposited under accession number NCIMB 42340.

In one aspect the invention relates to an isolated protein having a Serine 36 to Phenylalanine (S36F) substitution in SEQ ID NO: 1 or in variants of SEQ ID NO: 1, said variants having at least 85% amino acid sequence identity with SEQ ID NO: 1 and having said S36F amino acid substitution, or the equivalent amino acid position in a variant C1MBP 17_2 protein. In another aspect, the invention relates to a cDNA or mRNA or genomic DNA encoding such a protein.

In one embodiment of the invention (cDNA or genomic) nucleic acid sequences are provided encoding a mutant C1MBP 17_2 protein of the invention comprising one or more non-sense and/or missense mutations, e.g. transitions (replacement of purine with another purine (A⇆G) or pyrimidine with another pyrimidine (C⇆T)) or transversions (replacement of purine with pyrimidine, or vice versa (C/T⇆A/G). In one embodiment the non-sense and/or missense mutation(s) is/are in the nucleotide sequence encoding any of the C1MBP 17_2 exons. In one aspect the non-sense and/or missense mutation(s) is/are in the nucleotide sequence encoding exon 1 (amino acids 1 to 60 of SEQ ID NO: 1) of the MADS domain of exon 1 (amino acids 2 to 58 of SEQ ID NO: 1).

In yet another embodiment nucleic acid sequences are provided having at least 75% nucleic acid sequence identity with SEQ ID NO: 2 or 3 and comprising a cytosine to thymine substitution at position 107 of SEQ ID 2 or at position 1116 of SEQ ID NO: 3. In still another embodiment such nucleic acid sequences have at least 80% (e.g. 85%, 90%, 91%, 92%, 93%, 94%, 95%, 96%, 97%, 98%, 99% or even at least 99.5%, or at least 99.8% or at least 99.9% nucleic acid sequence identity with SEQ ID NO: 2 or 3 and comprising a cytosine to thymine substitution at position 107 of SEQ ID 2 or at position 1116 of SEQ ID NO: 3.

In still another embodiment nucleic acid sequences are provided hybridizing under stringent conditions with SEQ ID NO: 2 or 3 and comprising a cytosine to thymine substitution at position 107 of SEQ ID 2 or at position 1116 of SEQ ID NO: 3.

In another embodiment nucleic acid sequences are provided hybridizing under stringent conditions with SEQ ID NO: 2 and comprising a cytosine to thymine substitution at position 107 of SEQ ID 2 or parts thereof comprising a C to T substitution at a position corresponding to position 107 of SEQ ID NO: 2, counting A in the ATG of the START CODON as nucleotide position 1.

In yet another aspect, the invention relates to nucleic acid sequences encoding a cDNA having at least 75% nucleic acid sequence identity with SEQ ID NO: 2 and comprising a cytosine to thymine substitution at position 107 of SEQ ID 2 or parts thereof comprising a C to T substitution at a position corresponding to position 107 of SEQ ID NO: 2, counting A in the ATG of the START CODON as nucleotide position 1. In still another embodiment such nucleic acid sequences have at least 80% (e.g. 85%, 90%, 91%, 92%, 93%, 94%, 95%, 96%, 97%, 98%, 99% or even at least 99.5%, or at least 99.8% or at least 99.9% nucleic acid sequence identity with SEQ ID NO: 2 and comprising a cytosine to thymine substitution at position 107 of SEQ ID 2 or parts thereof comprising a C to T substitution at a position corresponding to position 107 of SEQ ID NO: 2, counting A in the ATG of the START CODON as nucleotide position 1.

In still another aspect the invention relates to a nucleic acid sequence according to SEQ ID NO: 5. In one aspect the invention relates to parts of the nucleic acid sequence of SEQ ID NO: 5 comprising the thymine (T) at position 107 or at a position corresponding to position 107 of SEQ ID NO: 5, counting A in the ATG of the START CODON as nucleotide position 1. Such parts can be of various lengths e.g. 8, 9, 10, 11, 12, 13, 14, 15, 16, 17, 18, 19, 20 nucleotides or even more e.g. 25, 30, 35, 40, 50, 60 nucleotides. It is understood that the required thymine at position 107 or at a position corresponding to position 107 of SEQ ID NO: 5 can be at position in such a fragment, e.g. in the beginning, about in the middle or towards the end of such fragment.

The sequences of the C1MBP 17_2 allele provided herein, or parts of these sequences (e.g. the specific mutations), can be used to select plants, plant tissues or plant parts comprising wild type or mutant alleles, and thus to select and/or generate watermelon plants or plant parts with high texture fruit phenotype. Alternatively, other molecular markers may be developed which are linked to the mutant C1MBP 17_2 allele and then selection of the high texture fruit flesh growth habit may be done by selecting for plants having the linked molecular markers. Linked markers can be developed using a range of techniques, such as Bulk Segregant Analysis, and a range of markers, such as AFLP markers, RFLP markers, SNP markers, mini- or micro-satellite markers, etc. For marker development a segregating population can be generated by e.g. crossing a plant having a high texture fruit flesh growth type (e.g. a diploid) with a plant having a normal fruit texture phenotype (e.g. a control) and developing segregating population therefrom (e.g. an F2 or F3 population or backcross population). Markers can then be identified which are closely associated (linked) with the high texture fruit flesh growth habit and the mutant C1MBP 17_2 allele, i.e. co-segregates with the allele. See for example Wolukau et al. (HortScience February 2009 vol. 44 no. 1 32-34) the use of Bulk Segregant Analysis in melon to identify markers linked to a resistance gene. A molecular marker is a DNA sequence or single nucleotide polymorphism (SNP) which is found on the chromosome close to the C1MBP 17_2 allele (e.g. within a genetic distance of 5 cM or less). Thus, in one embodiment the mutant C1MBP 17_2 allele can be introduced into other watermelon plants lacking the mutant C1MBP 17_2 allele by marker assisted breeding methods, using a molecular marker closely linked to the mutant C1MBP 17_2 allele.

One aspect of the invention relates to the use of a mutation a nucleotide sequence encoding a mutant protein of SEQ ID NO: 1 as a marker to identify or select a plant or plant part comprising a mutant C1MBP 17_2 allele and optionally plants capable of producing fruits with a high texture phenotype.

A method for screening plants or plant parts for the presence of a mutant C1MBP 17_2 allele is provided, comprising testing the plants or plant parts for the presence of a mutation in the nucleotide sequence encoding SEQ ID NO: 1, whereby the protein of SEQ ID NO: 1 comprises one or more amino acids inserted, deleted or replaced.

Once a plant comprising a mutant C1MBP 17_2 allele has been identified one can test whether the allele enhances fruit texture by e.g. selfing the plant to generate a plant homozygous for the mutant allele and then growing such plants together with suitable controls to test the fruit texture phenotype.

In another aspect the invention relates to the use as a marker, of a C to T substitution at position 107 of SEQ ID NO: 2, or at position 1116 of SEQ ID NO: 3.

In still another aspect the invention relates to the use as a marker, of a C to T substitution at position 107 of SEQ ID NO: 2, or at position 1116 of SEQ ID NO: 3 to identify watermelon plants or plant parts comprising a mutant C1MBP 17_2 allele.

In still another aspect of the invention watermelon plants are provided that have the same or similar firmer fruit flesh and/or reduced leakage of watermelon fruit parts and/or longer shelf-life of the fruits and/or a firmer watermelon rind as watermelon plants of the invention, of which representative seeds were deposited by Nunhems B.V. and accepted for deposit on 28 Nov. 2014 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit numbers: NCIMB 42340.

In one aspect, the invention relates to mutant 39. In another aspect the invention relates to breeding with mutant 39. In another aspect progeny (e.g. F1, F2, F3, F4 or further generation progeny) of mutant 39 comprising the mutant C1MBP 17_2 allele of mutant 39 is provided.

The mutant C1MBP 17_2 allele can be introduced into other watermelon plants lacking the mutant C1MBP 17_2 allele using known breeding methods. Known breeding methods can be used alone or in combination, such as (but not limited to) recurrent selection, pedigree breeding, backcross breeding, inbred development, hybrid testing, marker assisted breeding, etc. Progeny are then selected which retain the high texture fruit flesh, which can be easily identified phenotypically. Thus, selection of progeny plants having the high texture fruit flesh growth habit can be done by phenotypic selection of the high texture fruit flesh growth habit characteristics and by discarding plants which do not have the high texture fruit flesh growth habit characteristics.

As the mutant C1MBP 17_2 allele is recessive, the high texture fruit flesh phenotype may only be seen if no dominant C1MBP 17_2 allele is present. When transferring the C1MBP 17_2 allele from a diploid seed deposit made herein (e.g. NCIMB 42340 or progeny thereof) to another watermelon plant which does not contain the recessive C1MBP 17_2 allele, the F1 will be heterozygous and will not display the high texture fruit flesh phenotype and the breeder first needs to self the F1 to identify plants comprising the this high texture fruit flesh phenotype. Likewise, when transferring the C1MBP 17_2 allele from a tetraploid watermelon plant to another tetraploid watermelon plant not comprising the recessive C1MBP 17_2 allele, the F1 will be heterozygous and not display the high texture fruit flesh phenotype and again the high texture fruit flesh phenotype will only be seen in the F2 generation. A tetraploid plant comprising a high texture fruit phenotype can be generated by doubling the chromosomes of a diploid plant homozygous for the mutant allele (e.g. mutant 39, deposited under NCIMB 42340) to generate a tetraploid comprising four copies of the mutant allele. A diploid high texture fruit flesh plant can also be regenerated from the haploid cells of a tetraploid high texture fruit flesh plant (e.g. pollen or another culture and regeneration of a plant) and the derived diploid high texture fruit flesh plant may then be used in further breeding and in generating watermelon plants having a high texture fruit flesh phenotype. This may be referred to as a haploid tetraploid plant having a high texture fruit flesh phenotype. Such plants are encompassed herein.

Also seedlings, scions and rootstocks, as well as cells and tissues, and cell cultures and tissue cultures, and vegetative propagations of the plants comprising one or more mutant C1MBP 17_2 alleles in their genome, i.e. alleles which, when in homozygous form, lead to fruits having a high texture fruit flesh phenotype are encompassed herein. Thus whole plants obtained from seedlings, scions and rootstocks, as well as cells and tissues, cell cultures and tissue cultures and vegetative propagations of the plants retaining at least one mutant C1MBP 17_2 allele according to the invention are provided herein.

A method for generating a tetraploid inbred plant is provided, comprising the steps of:

a. providing a diploid plant comprising a mutant C1MBP 17_2 allele according to the invention;
b. optionally selfing said diploid plant for several generations to generate an inbred line;
c. doubling the chromosomes of said inbred line to generate a tetraploid line;
d. optionally selfing the tetraploid line for several generations.

Thus, in step a) the diploid plant may be any diploid watermelon plant comprising one or two copies of a mutant C1MPB 17_2 allele as described herein. In one aspect the diploid plant is a plant derived from seed deposited under NCIMB 42340 or progeny thereof, or may be a diploid plant into which the mutant C1MBP 17_2 allele from seed deposit NCIMB 42340 has been transferred by crossing and selection of the high texture fruit flesh growth type. The diploid may be a double-haploid plant generated by chromosome doubling of haploid cells of a plant, e.g. of a plant grown from seed deposited under NCIMB 42340.

Also provided is a method for producing triploid hybrid watermelon seeds, wherein triploid plants grown from such seeds produce fruits with high texture, said method comprising:

a. providing a diploid watermelon plant comprising two copies of a mutant C1MBP 17_2 allele of the invention and a tetraploid plant having four copies of a mutant C1MBP 17_2 allele of the invention,
b. allowing pollination of pistillate flowers of the tetraploid plant with pollen of the diploid plant, and
c. harvesting seeds produced in the fruits of the tetraploid plant, and optionally
d. drying the harvested seeds.

Optionally the dried and harvested F1 seeds are then packaged. They may also be treated prior to packaging. Thus packages or containers comprising or consisting of seeds obtained by the above method are an embodiment herein. Pollination may be by hand or by insects (e.g. bees) in isolation blocks. To ensure pollination of the tetraploid female flowers with pollen from the male diploid, different methods can be used, such as collecting male flowers by hand and hand-pollinating female flowers, followed by covering the pollinated flower. Alternatively, all male (staminate) flowers that develop on the tetraploid plants may be removed to ensure pollination of the pistillate flowers on the tetraploid high texture fruit flesh plants with diploid pollen of the diploid high texture fruit flesh plants. When the fruits on the tetraploid plants are mature, they are harvested and the triploid F1 hybrid seeds (resulting from cross-pollination) are collected. These may then be sorted (e.g. by size), dried, optionally treated, and packaged for sale. In one embodiment the diploid parent of a. is obtainable from seeds deposited under NCIMB 42340 or progeny or vegetative propagations thereof.

Also provided is a method of producing triploid watermelon fruits having a high texture fruit phenotype, comprising:

A) growing a triploid watermelon plant comprising three copies of a mutant C1MBP 17_2 allele of the invention;
B) allowing pollination of flowers of said triploid plant with pollen of a diploid pollenizer;

C) optionally harvesting fruits from said triploid watermelon plant.

In the above method triploid plants and diploid pollinizer plants may be interplanted. The pollinizer may be a dedicated pollinizer or a dual purpose pollinizer as described in WO2012069539. Thus, optionally also the diploid fruits of the pollinizer plant may also be harvested. In another aspect of the invention a cell culture or a tissue culture of regenerable cells of a plant having a high texture fruit flesh growth habit or comprising one or more mutant C1MBP 17_2 alleles, all as described above, is provided. A cell culture or a tissue culture comprises cells or protoplasts or plant tissue from a plant part of a plant comprising one or more mutant C1MBP 17_2 alleles (such as a high texture fruit flesh tetraploid, high texture fruit flesh diploid or high texture fruit flesh triploid plant, all as described herein) selected from the group consisting of: embryos, meristems, cotyledons, pollen, leaves, anthers, roots, root tips, pistils, flowers, seed, stalk. The plant part may be selected from a scion, fruit, pollen, ovule, stem, cotyledon, leaf, cell embryos, meristems, anthers, roots, root tips, pistils, flowers, seed. Also provided is a watermelon plant regenerated from such a cell culture or tissue culture, wherein the regenerated plant (or progeny thereof, e.g. obtained after selfing) comprises a high texture fruit flesh growth habit or comprising one or more mutant C1MBP 17_2 alleles. Therefore, in one aspect vegetatively propagated watermelon plants obtained from plant tissue of seeds or plants grown from seeds deposited under NCIMB 42340 are encompassed herein.

It is understood that it is also an object of the invention to provide seeds from which a diploid, triploid or tetraploid plant comprising one or more mutant C1MBP 17_2 alleles and optionally capable of producing fruits with the high texture fruit flesh phenotype described herein, can be grown. Also seedlings, scions and rootstocks, as well as cells and tissues of the diploid, triploid or tetraploid plants are encompassed herein. Such plant parts comprise the genetic determinants, i.e. at least one mutant C1MBP 17_2 allele, for producing high texture fruit flesh plants according to the invention. Thus whole plants obtained from seedlings, scions and rootstocks, as well as from cells and tissues of the diploid, triploid or tetraploid plants, retain the mutant C1MBP_17_2 allele(s) of the invention.

Watermelon seeds containing a mutant C1MBP 17_2 allele according to the invention are provided, wherein a representative sample of seeds containing the allele have been deposited under accession number NCIMB 42340. Also provided is a watermelon plant produced by growing said seeds. Also pollen and ovules of the plant produced by growing said seeds is provided.

Watermelon plants obtained (derived), or obtainable (derivable), from plants according to the invention (e.g. from plants comprising a high texture fruit flesh phenotype and/or comprising one or more mutant C1MBP 17_2 alleles, which confers the high texture fruit flesh phenotype when in homozygous form) include plants obtained by breeding methods, such as selfing, crossing, backcrossing, recurrent selection, double haploid production, marker assisted selection, clonal propagations, transformants, etc., whereby the derived plants comprise a high texture fruit flesh phenotype and/or the genetic determinants (one or more mutant C1MBP 17_2 alleles) which confers the high texture fruit flesh growth habit according to the invention when the allele is in homozygous form, i.e. when no functional wild type C1MBP 17_2 allele is present in the genome.

Also fruit of a watermelon plant is provided, wherein the fruit is produced by self-pollination of the plant.

In Examples 3 and 4 measurements of flesh firmness and juice leakage were done.

In one embodiment the plant of the invention therefore has produce fruits which have an average fruit flesh firmness at harvest at the center (M1) of transversely cut-in-halves fruits that is at least 15%, preferably at least 20%, 25%, 30%, 35%, 40%, 45%, 50%, 55%, 60%, 65%, 70%, 80%, 90%, 100%, 120%, or even at least 125% higher than the average fruit flesh firmness of fruits of wild type plants.

In one embodiment the plant of the invention therefore has produce fruits which have an average fruit flesh firmness 20 days after harvest of the ripe fruits at the center (M1) of transversely cut-in-halves fruits that is at least 15%, preferably at least 20%, 25%, 30%, 35%, 40%, 45%, 50%, 55%, 60%, 65%, 70%, 80%, 90%, 100%, 120%, or even at least 125% higher than the average fruit flesh firmness of fruits of wild type plants.

In one embodiment the plant of the invention therefore has produce fruits which have an average fruit flesh firmness 40 days after harvest of the ripe fruits at the center (M1) of transversely cut-in-halves fruits that is at least 15%, preferably at least 20%, 25%, 30%, 35%, 40%, 45%, 50%, 55%, 60%, 65%, 70%, 80%, 90%, 100%, 120%, or even at least 125% higher than the average fruit flesh firmness of fruits of wild type plants.

In one embodiment the plant of the invention therefore has produce fruits which have an average fruit flesh firmness at harvest of the ripe fruits at the interlocular tissue (M2-M3-M4)) of transversely cut-in-halves fruits that is at least 15%, preferably at least 20%, 25%, 30%, 35%, 40%, 45%, 50%, 55%, 60%, 65%, 70%, 80%, 90%, 100%, 120%, or even at least 125% higher than the average fruit flesh firmness of fruits of wild type plants.

In one embodiment the plant of the invention therefore has produce fruits which have an average fruit flesh firmness 20 days after harvest of the ripe fruits at the interlocular tissue (M2-M3-M4)) of transversely cut-in-halves fruits that is at least 15%, preferably at least 20%, 25%, 30%, 35%, 40%, 45%, 50%, 55%, 60%, 65%, 70%, 80%, 90%, 100%, 120%, or even at least 125% higher than the average fruit flesh firmness of fruits of wild type plants.

In one embodiment the plant of the invention therefore has produce fruits which have an average fruit flesh firmness 40 days after harvest of the ripe fruits at the interlocular tissue (M2-M3-M4)) of transversely cut-in-halves fruits that is at least 15%, preferably at least 20%, 25%, 30%, 35%, 40%, 45%, 50%, 55%, 60%, 65%, 70%, 80%, 90%, 100%, 120%, or even at least 125% higher than the average fruit flesh firmness of fruits of wild type plants.

In one aspect the invention further relates to a plant of the invention i.e. a plant of the species *Citrullus lanatus* var. *lanatus* wherein the plant comprises one or more mutations in the *Citrullus lanatus* Mads Box Protein 17_2 (C1MBP 17_2) allele wherein the fresh fruits have a lower fruit leakage at 18 days after harvest as compared to wild type plants. In one embodiment of this aspect the leakage of the inner parts is reduced by at least 25%, e.g. at least 30%, 35%, 40%, 45%, 50%, 55%, 60%, 65%, 70% or even at least 75% of the WT plants inner fruit parts. In another embodiment of this aspect the leakage of the outer parts is reduced by at least 25%, e.g. at least 30%, 35%, 40%, 45%, 50%, 55%, 60%, 65%, 70%, 75%, 80% or even at least 85% of the WT plants inner fruit parts.

In one aspect the invention further relates to a plant of the invention i.e. a plant of the species *Citrullus lanatus* var. *lanatus* wherein the plant comprises one or more mutations in the *Citrullus lanatus* Mads Box Protein 17_2 (C1MBP 17_2) allele wherein the fresh fruits have a lower fruit leakage at 18 days after harvest as compared to wild type plant wherein the plant comprises one copy of the C1MBP17_2 as present in seeds deposited under NCIMB 42340. In one embodiment of this aspect the leakage of the inner parts is reduced by at least 25%, e.g. at least 30%, 35%, 40%, 45%, 50%, 55%, 60%, 65%, 70% or even at least 75% of the WT plants inner fruit parts. In another embodiment of this aspect the leakage of the outer parts is reduced by at least 25%, e.g. at least 30%, 35%, 40%, 45%, 50%, 55%, 60%, 65%, 70%, 75%, 80% or even at least 85% of the WT plants inner fruit parts. In these aspects, juice leakage can be recorded as described herein.

In another aspect, the invention further relates to a plant of the invention i.e. a plant of the species *Citrullus lanatus* var. *lanatus* wherein the plant comprises one or more mutations in the *Citrullus lanatus* Mads Box Protein 17_2 (C1MBP 17_2) allele wherein the fresh fruits inner parts have a fruit leakage at 18 days after harvest of less than 4%, e.g. less than 3% or even less than 2%. Juice leakage can be calculated as described herein.

In another aspect, the invention further relates to a plant of the invention i.e. a plant of the species *Citrullus lanatus* var. *lanatus* wherein the plant comprises one or more mutations in the *Citrullus lanatus* Mads Box Protein 17_2 (C1MBP 17_2) allele wherein the fresh fruits outer parts have a fruit leakage at 18 days after harvest of less than 7%, e.g. less than 6%, 5%, 4% or even less than 3%. Juice leakage can be calculated as described herein.

In a preferred aspect, the plant comprises one copy of the C1MBP17_2 as present in seeds deposited under NCIMB 42340.

Figure 6:
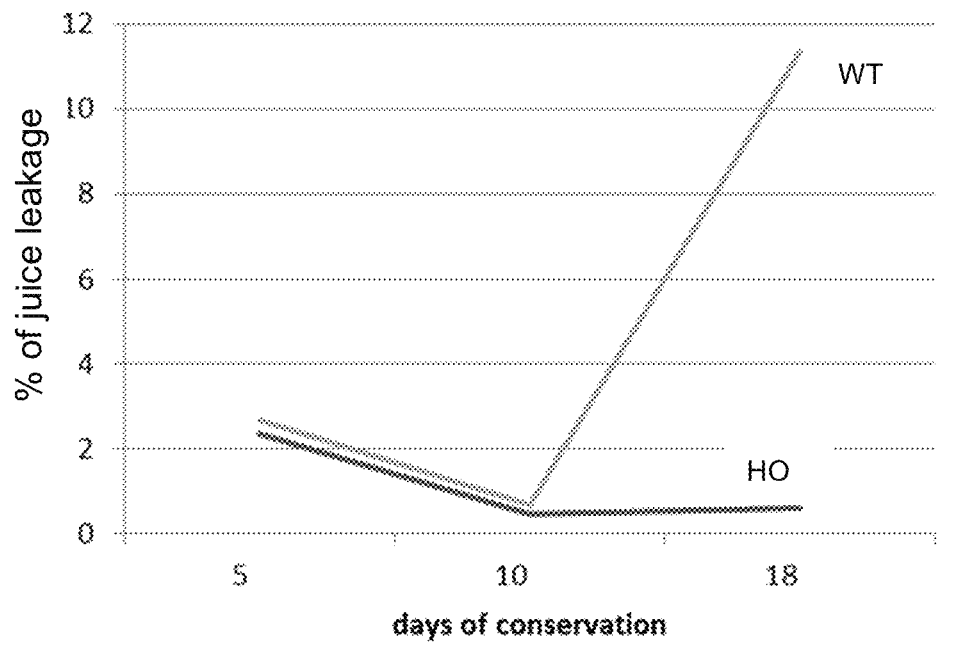
FIG. 6 shows the percentage juice leakage of the inner part of 20-day conserved ripe watermelon fruits of WT, and fruits homozygous (HO) for the mutant C1MBP17_2 allele of the invention at A) 5, 10, and 18 days after harvest and B) the total juice leakage of inner part.
Figure 6:
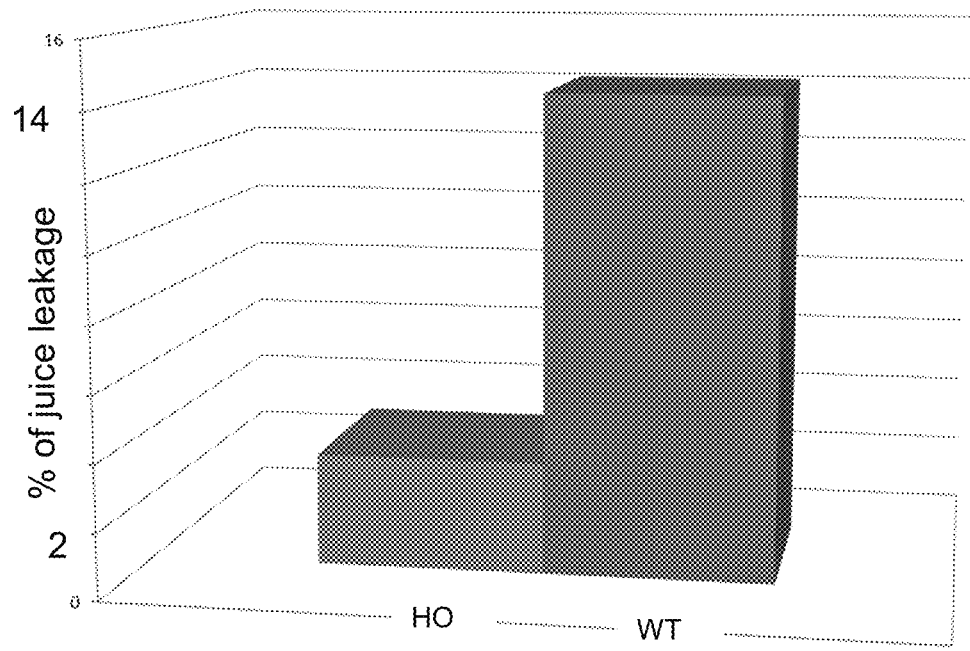
Figure 7:
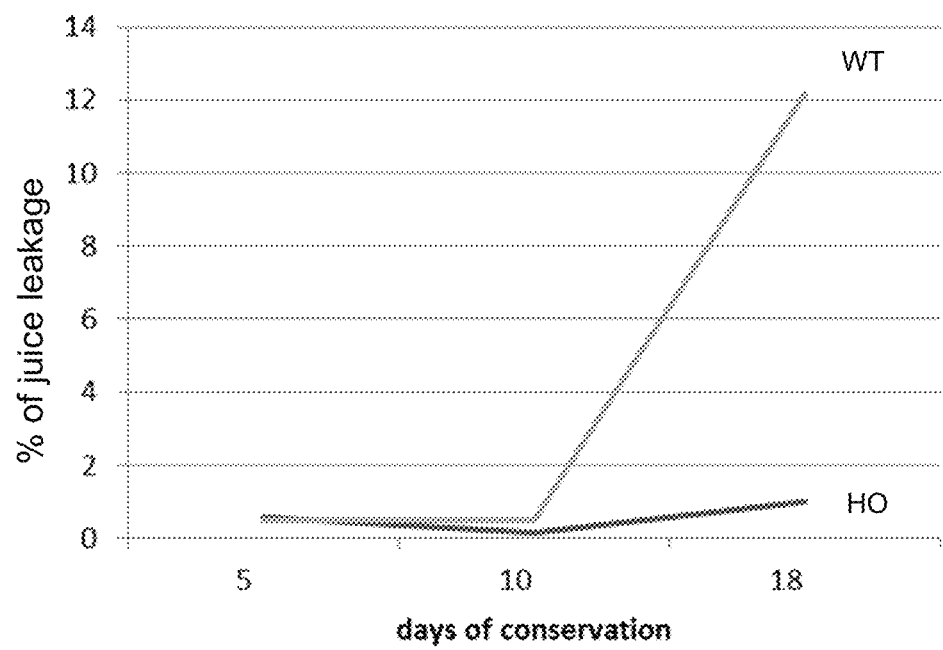
FIG. 7 shows the percentage juice leakage of the outer part of 20-day conserved ripe watermelon fruits of WT, and fruits homozygous (HO) for the mutant C1MBP17_2 allele of the invention at A) 5, 10, and 18 days after harvest and B) the total juice leakage of outer part.
Figure 7:
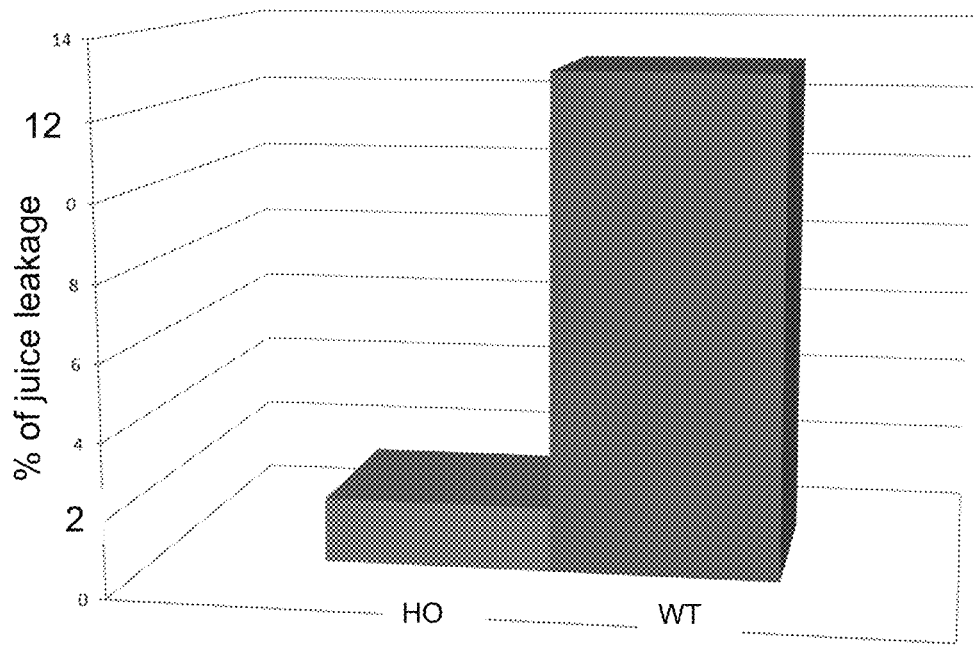

Juice leakage data for inner and outer parts of 20 day conserved fruits is shown in FIGS. 6 and 7, respectively. These figures show that fruits homozygous (HO) for the mutant C1MBP17_2 allele of the invention have a juice leakage which is lower than that of wild type fruits. Especially 38 days post harvest. After 38 days (i.e. 20 days conservation+18 days juice leakage experiment), juice leakage of HO fruits inner parts is about 16% of WT fruits for the inner parts (2.2 vs 14 gr), while HO outer parts only have a juice leakage of 8% compared to WT (1 vs 12.2 gr).

In one aspect the invention further relates to a plant of the invention i.e. a plant of the species *Citrullus lanatus* var. *lanatus* wherein the plant comprises one or more mutations in the *Citrullus lanatus* Mads Box Protein 17_2 (C1MBP 17_2) allele wherein 20 day conserved fruits have a lower fruit leakage at 38 days after harvest (i.e. 20 conservation+ 18 days juice leakage experiment) as compared to wild type plants. In one embodiment of this aspect the leakage of the inner parts is reduced by at least 25%, e.g. at least 30%, 35%, 40%, 45%, 50%, 55%, 60%, 65%, 70%, 75%, 80% or even at least 82% of the WT plants inner fruit parts. In another embodiment of this aspect the leakage of the outer parts is reduced by at least 25%, e.g. at least 30%, 35%, 40%, 45%, 50%, 55%, 60%, 65%, 70%, 75%, 80%, 85%, or even at least 90% of the WT plants outer fruit parts. Preferably said plant is homozygous for the recited mutant allele.

In one aspect the invention further relates to a plant of the invention i.e. a plant of the species *Citrullus lanatus* var. *lanatus* wherein the plant comprises one or more mutations in the *Citrullus lanatus* Mads Box Protein 17_2 (C1MBP 17_2) allele wherein 20 day conserved fruits have a lower fruit leakage at 38 days after harvest (i.e. 20+18 days) as compared to wild type plant wherein the plant comprises one copy to the C1MBP17_2 as present in seeds deposited under NCIMB 42340. In one embodiment of this aspect the leakage of the inner parts is reduced by at least 25%, e.g. at least 30%, 35%, 40%, 45%, 50%, 55%, 60%, 65%, 70%, 75%, 80%, or even at least 82% of the WT plants inner fruit parts. In another embodiment of this aspect the leakage of the outer parts is reduced by at least 25%, e.g. at least 30%, 35%, 40%, 45%, 50%, 55%, 60%, 65%, 70%, 75%, 80%, 85%, or even at least 90% of the WT plants outer fruit parts. Preferably said plant is homozygous for the recited mutant allele.

Seed Deposit

A representative sample of seeds of a mutant plant according to the invention as shown in example 2 were deposited by Nunhems B.V. and accepted for deposit on 28 Nov. 2014 at the NCIMB Ltd. (Ferguson Building, Craibstone Estate, Bucksburn Aberdeen, Scotland AB21 9YA, UK) according to the Budapest Treaty, under the Expert Solution (EPC 2000, Rule 32(1)). Seeds were given the following deposit number: NCIMB 42340.

The Applicant requests that samples of the biological material and any material derived therefrom be only released to a designated Expert in accordance with Rule 32(1) EPC or related legislation of countries or treaties having similar rules and regulation, until the mention of the grant of the patent, or for 20 years from the date of filing if the application is refused, withdrawn or deemed to be withdrawn.

Access to the deposit will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

EXAMPLES

General Methods

PCR amplification products were directly sequenced by a service company (BaseClear, The Netherlands, world wide web at baseclear.com/) using the same primers as were used for the amplification. The obtained sequences were aligned using a computer program (CLC Bio Main Work Bench, Denmark, world wide web at cicbio.com) to identify the nucleotide changes.

Materials

Water used for analyses and mutagenesis is tap water filtered in an Milli-Q water Integral system, Milli-Q type Reference A+ supplied with a Q-gard T2 Cartridge and a Quantum TEX Cartridge. Water resistance is >=18 MOhm.

Ethyl Methanesulfonate (EMS) (pure) was obtained from Sigma, product number M0880.

Example 1

Mutagenesis

A highly homozygous (proprietary) inbred line used in commercial watermelon breeding was used for mutagenesis treatment with the following protocol. Two batches of 10000 seeds respectively, were each soaked in 1000 ml of ultrapure water and ethyl methanesulfonate (EMS) in conical flasks. The flasks were shaken several hours. EMS was rinsed out under flowing water. Following EMS treatment, seeds were sown in the greenhouse. Plantlets obtained out of the seeds that germinated, were transplanted in the field 3 to 4 weeks after sowing. On the fertile plants, just before opening, female flower buds were covered with a paper bag to prevent cross pollinations by insects. Fully opened female flowers were pollinated using pollen from a young male flower derived from the same branch of the plant. For each M1 mutant plant one or two fruits were harvested and its seeds isolated. Each seed lot in the obtained M2 population, represented one M2 family.

From each of the M2 seed packets 5 seeds were taken and sown on soil for DNA extraction. From each of the 5 seedlings a punch (5 mm disk) from one cotyledon was taken and pooled for DNA isolation. DNA was isolated using a commercial DNA isolation system DNeasy 96 Plant Kit, Qiagen, Venlo, Netherlands), followed by multiplex PCRs for mutation detection analysis.

Primers used to amplify gene fragments for High Resolution Melt curve analysis (HRM) were designed using a computer program (Primer3, primer3.sourceforge.net). The length of the amplification product was limited between 200 and 400 base pairs. Quality of the primers was determined by a test PCR reaction that should yield a single product.

Polymerase Chain Reaction (PCR) to amplify gene fragments. 4.8 ng of genomic DNA (4 µl) was mixed with 4 µl reaction buffer (5× Reaction Buffer), 2 µl 10×LCGreen dye ((LCGreen Plus+ Melting Dye, Idaho Technology Inc., UT, USA), 5 pmole of forward and reverse primers each, 4 nmole dNTPs (Life Technologies, NY, USA) and 1 unit DNA polymerase (Hot Start II DNA Polymerase) in a total volume of 20 µl. Reaction conditions were: 30 s 98° C., then 40 cycles of 10 s. 98° C., 15 s 60° C., 25 s of 72° C. and finally 60 s at 72° C.

High Resolution Melt curve analysis (HRM) is a non-enzymatic screening technique. During the PCR dye molecules (LCGreen Plus+ Melting Dye, Idaho Technology Inc., UT, USA) intercalate between each annealed base pair of the double stranded DNA molecule. When captured in the molecule, the dye emits fluorescence at 510 nm after excitation at 470 nm. A camera in a fluorescence detector (LightScanner, Idaho Technology Inc., UT, USA) records the fluorescence intensity while the DNA sample is progressively heated. At a temperature dependent on the sequence specific stability of the DNA helices, the double stranded PCR product starts to melt, releasing the dye. The release of dye results in decreased fluorescence that was recorded as a melting curve by the fluorescence detector. Pools containing a mutation form hetero duplexes in the post-PCR fragment mix were identified as differential melting temperature curves in comparison to homo duplexes.

The presence of the particular mutation in individual plants was confirmed by repeating the HRM analysis on DNA from the individual M2 seed lots of the identified corresponding DNA pool. When the presence of the mutation, based on the HRM profile, was confirmed in one of the four individual M2 family DNA samples, the PCR fragments were sequenced to identify the mutation in the gene.

Once the mutation was known, the effect of such an mutation was predicted using a computer program SIFT (Sorting Tolerant From Intolerant, P. Kumar, S. Henikoff & P. C Ng, Nature Protocols 2009 4, 1073-1082).

Seeds from M2 families that were selected using SIFT were sown in trays in 80% humus—20% vermiculite substrate. From the DNA analysis homozygous and heterozygous plants were selected and then cultivated in an insect proof greenhouse. Plants were used for a backcross with the original inbred line in order to eliminate undesired mutation(s) from the genetic background. During this process a preliminary observation of the phenotype was carried out.

Backcross seeds were grown in greenhouse and plants were self-pollinated to recreate the homozygous status of the screened mutations. BC1S1 seed was harvested.

A large number of BC1S1 seeds was sown in trays and plants sampled for DNA analysis. Homozygous and azygous plants were selected for phenotyping experiment—azygous plants are plants with the same genotype as the mutant plants, except for the induced mutation(s) that is being investigated.

Selected plants were transplanted into the open field to grow them following the normal practices of watermelon growers. Plants were transplanted at beginning of May. At least 20 homozygous plants and 20 azygous plants for each mutant were transplanted. Plants were watered by drip irrigation and the crop management was done according to the specific technical recommendations for watermelon. Fruits were harvested 80 days after transplanting at their commercial ripening stage.

Harvested fruits were analyzed for flesh firmness using a penetrometer (FG500, PCE instruments) and for brix content using a refractometer (Pen-Pro, Atago, Japan). Visual assessment of other fruit parameters (external color, rind thickness, flesh color, seed size and color) completed the phenotypic evaluation.

Example 2

The firmness of the watermelon fruit flesh was measured using a precision dynamometer (PCE FG500, PCE Brookhuis B.V. The Netherlands). Fruits were cut transversally in halves and the firmness was measured at four locations of the fruit flesh. Data was collected from ripe fruits that were harvested on the same day. The first location was the center (central column) (i.e. referred as "Middle") of the fruit and the other three measurements were done on the interlocular tissue (M2, M3, M4) at about two-third of the radius from the center to the rind (See FIG. 2). For each measurement the dynamometer's tip (diameter 9 mm, flat point) was pushed 2.0 cm into the tissue and the necessary force was recorded. The value for firmness of the fruit is expressed in kilogram. To convert these values to $kg/cm^2$, the value was divided by 0.64 (tip surface being 0.64 $cm^2$), to convert it to $N/cm^2$, the $kg/cm^2$ value was multiplied by 9.80665 (i.e. kilogram to Newton conversion). One mutant plant was identified, referred to herein as mutant 39, which had a significantly higher fruit flesh firmness compared to the wild type when grown under the same conditions and harvested at the same time. Results of the measurements are given in Table 1 (individual plants) and Table 2 (average).

TABLE 1

Fruit firmness measurement [expressed in kg] of Wild Type (WT) and Mutant 39 fruit flesh

| Plant | Fruit | Middle | Interlocular tissue | | | Average M2-M4 |
|---|---|---|---|---|---|---|
| | | | M2 | M3 | M4 | |
| Plant 1 Mutant 39 | 1 | 4.61 | 2.19 | 2.49 | 1.45 | 2.04 |
| | 2 | 6.18 | 3.06 | 3.92 | 2.29 | 3.09 |
| | 3 | 6.04 | 3.27 | 2.59 | 2.18 | 2.68 |
| | average | 5.61 | 2.84 | 3.0 | 1.97 | 2.60 |
| Plant 2 Mutant 39 | 1 | 6.29 | 2.89 | 2.28 | 2.38 | 2.52 |
| | 2 | 3.18 | 1.8 | 1.61 | 1.86 | 1.76 |
| | 3 | 3.47 | 2.18 | 2.35 | 1.91 | 2.15 |
| | average | 4.31 | 2.29 | 2.08 | 2.05 | 2.14 |
| Plant 3 Mutant 39 | 1 | 6.25 | 2.37 | 1.57 | 3.25 | 2.40 |
| | 2 | 5.62 | 2.33 | 1.7 | 2.55 | 2.19 |
| | 3 | 2.84 | 1.33 | 1.97 | 2.6 | 1.97 |
| | average | 4.90 | 2.01 | 1.74 | 2.8 | 2.18 |
| | Overall average of mutant 39 | 4.94 | 2.38 | 2.27 | 2.27 | 2.31 |
| Plant 1 - WT | 1 | 2.25 | 1.17 | 1.34 | 1.67 | 1.39 |
| | 2 | 2.6 | 2.0 | 1.76 | 1.71 | 1.82 |
| | average | 2.42 | 1.58 | 1.55 | 1.69 | 1.60 |
| Plant 2 - WT | 1 | 1.9 | 2.02 | 1.9 | 1.58 | 1.83 |
| | 2 | 2.01 | 1.61 | 1.8 | 1.42 | 1.61 |
| | average | 1.95 | 1.81 | 1.85 | 1.5 | 1.72 |
| Plant 3 - WT | 1 | 1.85 | 1.17 | 1.72 | 1.49 | 1.46 |
| | 2 | 1.21 | 0.98 | 0.9 | 1.6 | 1.16 |
| | average | 1.53 | 1.07 | 1.31 | 1.54 | 1.31 |
| | Overall average of WT | 1.97 | 1.48 | 1.57 | 1.57 | 1.55 |

TABLE 2

Average* firmness measurement of Wild Type (WT) and Mutant 39 fruit flesh

| Plant | Firmness middle | | | Firmness interlocular tissue | | |
|---|---|---|---|---|---|---|
| | kg | kg/cm² | N/cm² | kg | kg/cm² | N/cm² |
| Mutant 39 | 4.94 | 7.72 | 75.71 | 2.31 | 3.61 | 35.40 |
| WT | 1.97 | 3.08 | 30.20 | 1.55 | 2.42 | 23.73 |
| Firmness of Mutant relative to WT | 2.5 times WT | | | 1.49 times WT | | |

*Average mutant corresponds to overall average of 3 plants, 3 fruits per plant; average WT corresponds to overall average of 3 plants and 2 fruits per plant The results show that fruits of mutant 39 show an increased fruit firmness compared to WT plants. The average fruit firmness in the middle of the fruits is about 2.5 times as high as that of the WT fruits. While the average fruit firmness in the interlocular tissue is about 1.5 times as high as that of the wild type fruits. The increased fruit firmness leads to a reduced leakage of liquid from watermelon fruit parts when cut and stored. In addition, the increase fruit firmness likely leads to the fruits being less vulnerable to damages/cracking during harvest, transportation and storage.

Mutant 39 contained a mutant C1MBP 17_2 allele, encoding a mutant C1MBP 17_2 protein as shown in FIG. 1. The increased fruit firmness of mutant 39 was confirmed to be a result of the mutation.

Example 3

Starting from the a mutant plant comprising the mutant C1MBP17_2 allele, a BC1F2 population was generated by crossing the mutant plant with an internal breeding line not comprising the mutant C1MBP17_2 allele (recurrent parent). A progeny plant comprising the mutant C1MBP17_2 allele was back crossed with the internal breeding line. Progeny plants were selfed for two generations to get a BC1F2 population. Plants homozygous and heterozygous for the C1MBP17_2 allele were identified and labeled BC1F2 HO and BC1F2 Het, respectively.

BC1F2 HO (HO), BC1F2 Het (HET), and the recurrent parent plant lacking the mutant C1MBP17_2 allele (WT) were sown and grown in the 2015 growing season in Chili. Approximately 70 days after transplanting fruits were ready for harvest. Collected fruits were put in plastic boxes and stored in an open place under the shadow, at room temperature. Fruit firmness was measured of ripe fruits at harvest for each type of plant following the same protocol as described in Example 2. This time, fruit firmness was measured at the day of harvest (days after harvest=0) of the ripe fruits, and in addition, ripe fruits were stored for 20 and 40 days after harvest, and fruit firmness was determined 20 and 40 days after harvest. It is understood that individual fruits were only used once for a fruit firmness determination.

Brix was also determined using the following protocol: a complete slice of approx. 2 cm thickness was collected from the middle of the watermelon fruit. The rind was removed from the slice. The slice without rind was homogenized. Brix content was measured with an ATAGO PEN-PRO refractometer soaked into the juice obtained after the homogenization. Both wild type and plants comprising the mutant C1MBP17_2 allele (in homozygous or heterozygous form) had a brix value at harvest that is at least 7, (which is acceptable for commercial watermelon fruits).

Results of the measurements are given in Table 3 (individual fruits of individual plants) and Table 4 (average).

TABLE 3

| Fruit type | days after harvest | Firmness middle (M1) [in kg] | Firmness Interlocular tissue (average M2-M3-M4) [in kg] | Firmness Average M1-M2-M3-M4) [in kg] |
|---|---|---|---|---|
| WT | 0 | 1.22 | 1.07 | 1.11 |
| WT | 0 | 1.90 | 1.82 | 1.84 |
| WT | 0 | 1.90 | 1.34 | 1.32 |
| WT | 0 | 2.14 | 1.42 | 1.60 |
| WT | 0 | 1.59 | 1.10 | 1.23 |
| WT | 0 | 2.00 | 1.43 | 1.58 |
| HET | 0 | 2.10 | 1.16 | 1.40 |
| HET | 0 | 2.00 | 1.23 | 1.42 |
| HET | 0 | 2.39 | 1.11 | 1.43 |
| HET | 0 | 2.26 | 1.56 | 1.73 |
| HO | 0 | 5.13 | 3.72 | 4.07 |
| HO | 0 | 4.65 | 3.42 | 3.73 |
| HO | 0 | 2.78 | 2.10 | 2.27 |
| HO | 0 | 4.07 | 2.89 | 3.19 |
| HO | 0 | 2.72 | 2.37 | 2.46 |
| WT | 20 | 1.16 | 0.82 | 0.91 |
| WT | 20 | 1.38 | 0.82 | 0.96 |
| WT | 20 | 1.66 | 1.04 | 1.19 |
| WT | 20 | 1.55 | 1.31 | 1.37 |
| WT | 20 | 2.26 | 0.93 | 1.08 |
| HET | 20 | 3.13 | 1.47 | 1.89 |
| HET | 20 | 2.26 | 1.09 | 1.39 |
| HO | 20 | 3.88 | 2.64 | 2.95 |
| HO | 20 | 6.12 | 4.55 | 4.95 |
| HO | 20 | 4.51 | 2.35 | 2.89 |
| HO | 20 | 3.40 | 2.62 | 2.82 |
| HO | 20 | 2.26 | 2.21 | 2.62 |
| WT | 40 | 1.78 | 1.19 | 1.34 |
| WT | 40 | 1.49 | 1.31 | 1.40 |
| WT | 40 | 2.07 | 1.20 | 1.35 |
| WT | 40 * | | | |
| WT | 40 * | | | |

TABLE 3-continued

| Fruit type | days after harvest | Firmness middle (M1) [in kg] | Firmness Interlocular tissue (average M2-M3-M4) [in kg] | Firmness Average M1-M2-M3-M4 [in kg] |
|---|---|---|---|---|
| WT | 40 * | | | |
| HET | 40 | 1.49 | 1.10 | 1.20 |
| HET | 40 | 1.22 | 0.80 | 0.91 |
| HET | 40 | 2.07 | 0.98 | 1.25 |
| HET | 40 | 2.12 | 1.23 | 1.45 |
| HET | 40 | 1.49 | 1.25 | 1.34 |
| HET | 40 | 1.64 | 0.86 | 1.06 |
| HO | 40 | 3.23 | 2.02 | 2.32 |
| HO | 40 | 4.48 | 3.29 | 3.59 |
| HO | 40 | 4.23 | 3.39 | 3.60 |
| HO | 40 | 3.01 | 2.24 | 2.44 |
| HO | 40 | 3.45 | 2.11 | 2.44 |

* fruits were overripe, no firmness or brix was recorded.

TABLE 4

| Fruit type | Days after harvest | Firmness middle (M1) [in kg] | Firmness Interlocular tissue (average M2-M3-M4) [in kg] | Firmness Average M1-M2-M3-M4 [in kg] |
|---|---|---|---|---|
| WT | 0 | 1.79 | 1.36 | 1.45 |
| WT | 20 | 1.60 | 0.98 | 1.10 |
| WT | 40 | 1.78 | 1.23 | 1.36 |
| HET | 0 | 2.19 (+22%) | 1.27 (−7%) | 1.50 (+3%) |
| HET | 20 | 2.70 (+68%) | 1.28 (+30%) | 1.64 (+49%) |
| HET | 40 | 1.67 (−6%) | 1.04 (−16%) | 1.20 −12%) |
| HO | 0 | 3.87 (+77%) | 2.90 (+129%) | 3.14 (+110%) |
| HO | 20 | 4.03 (+50%) | 2.87 (+125%) | 3.25 (+98%) |
| HO | 40 | 3.68 (+120% | 2.61 (+152%) | 2.88 +140%) |

As can be seen from the data shown in Table 3 and Table 4, the mutant C1MBP17_2 allele of the current invention (of plants of the invention) has an impact on fruit firmness in homozygous and heterozygous state. See for example the average firmness [in kg] at harvest of heterozygous ripe fruits is increased with 22% in the center (M1), it is even further increase 20 days after harvest (increase of +68%. Fruit firmness of fruits homozygous for the mutant C1MBP17_2 allele is increased at M1 with 77% at harvest up to +120% 40 days after harvest. Likewise, the Fruit firmness of fruits homozygous for the mutant C1MBP17_2 allele is increased in the interlocular tissue (M2-M4) with +110% at harvest to +140% 40 days after harvest.

Example 4

Juice Leakage Determination

A further advantage of the plants of the current invention is that they better retain juice/liquids in the fruit flesh as is illustrated below.

Figure 3:
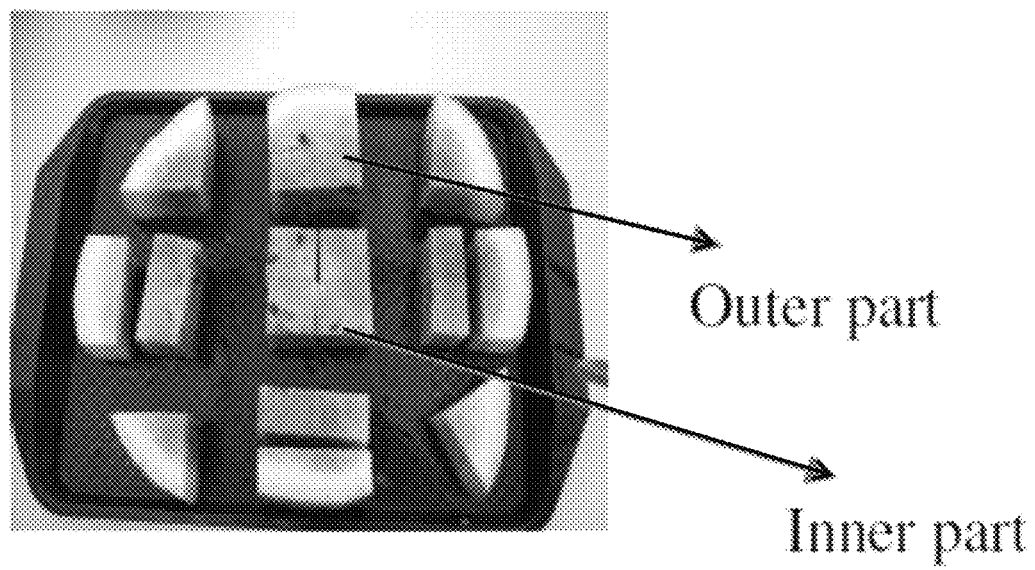

Protocol for juice leakage determination a. Fruit were harvested at commercial ripening (T0);

b. Fruit flesh cubes were collected in the inner part and in the outer part from a slice of approx. 3-4 cm of thickness as is indicated in FIG. 3;

c. Cubes were stored in a polypropylene box in a cold room at 4.5° C. Data was collected after 5-10 and 18 days of inner and outer parts separately;

d. Samples were weighted each time, then the juice was removed and weight measured again. The difference gives the juice leakage that was then expressed as % of the total weight.

So, for example 100 grams of cubes were collected in step b., after 5 days juice is removed, and 98 grams of cubes is left, i.e. 2% leakage. On the tenth day (day 10) after step b. (i.e. 5 days after the first juice removal) another r8 grams of juice is removed, i.e. 90 grams of cubes left. That means 8.15% leakage (8 gram out of 98 gram. 18 Days after step b (i.e. 13 days after first juice collection), 20 grams of juice is removed from the cubes. This would represent 20 gram of 90 gram equals 22% juice leakage.

The final or total juice leakage is the sum of the single losses (i.e. 2+8+20 gr) divided by the initial weight a T0 (100 gr) so 30% in the example provided above.

The same protocol was adopted on fruits 20 days after post-harvest storage at room temperature. In this case only mutant fruits homozygous for the mutant C1MBP17_2 of the invention and wild type fruits were analyzed.

Figure 4:
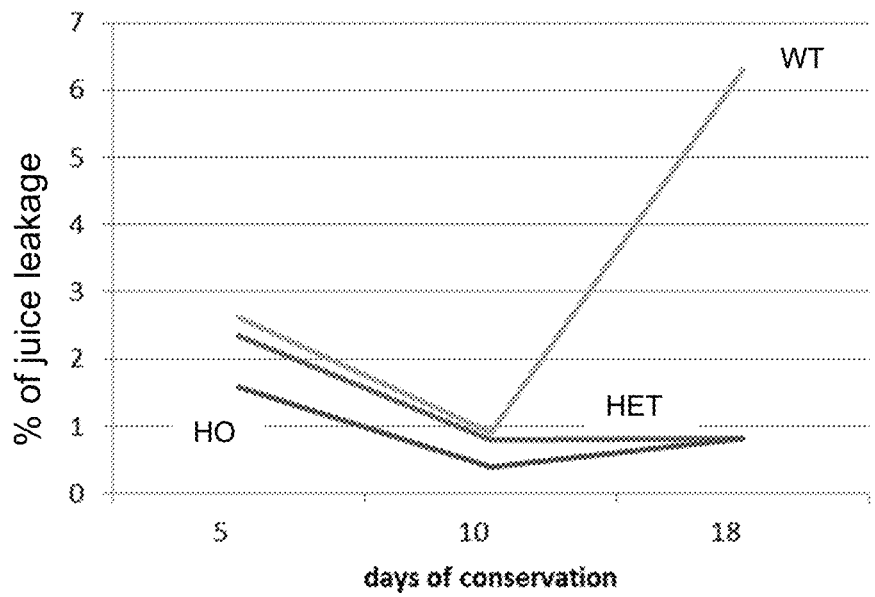
FIG. 4 shows the percentage juice leakage of the inner part of fresh ripe watermelon fruits of WT, and fruits homozygous (HO) and heterozygous (HET) for the mutant C1MBP17_2 allele of the invention at A) 5, 10, and 18 days after harvest and B) the total juice leakage of inner part.
Figure 4:
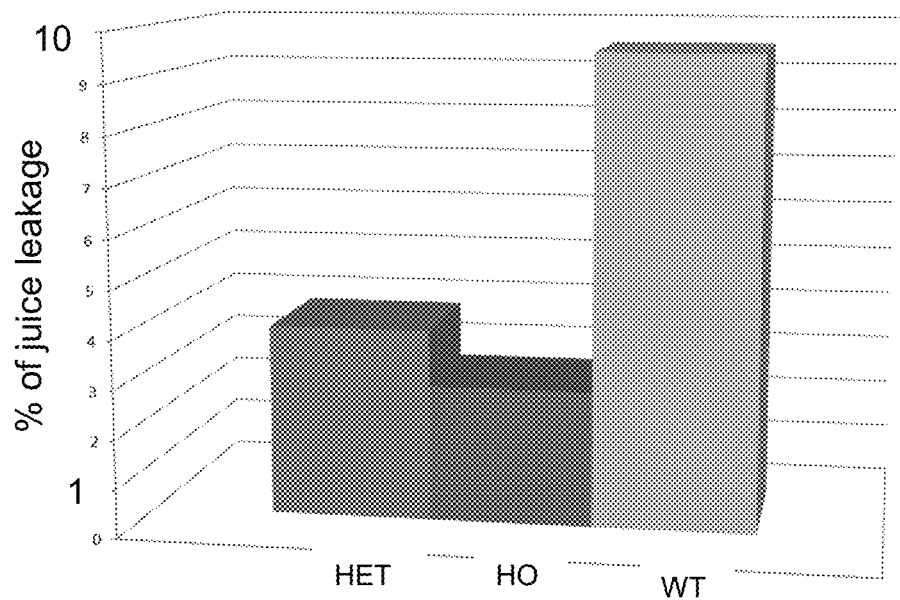
Figure 5:
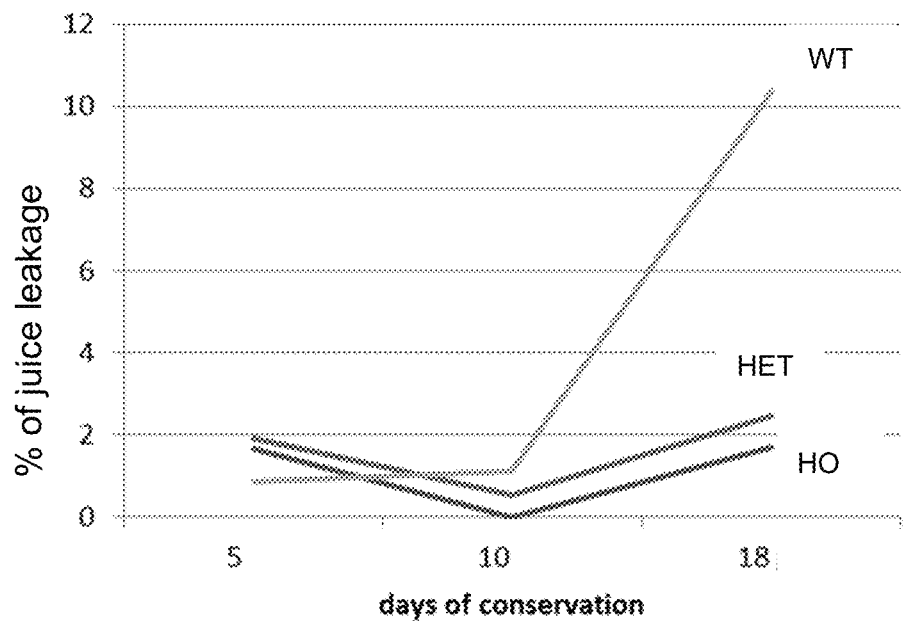
FIG. 5 shows the percentage juice leakage of the outer part of fresh ripe watermelon fruits of WT, and fruits homozygous (HO) and heterozygous (HET) for the mutant C1MBP17_2 allele of the invention at A) 5, 10, and 18 days after harvest and B) the total juice leakage of outer part.
Figure 5:
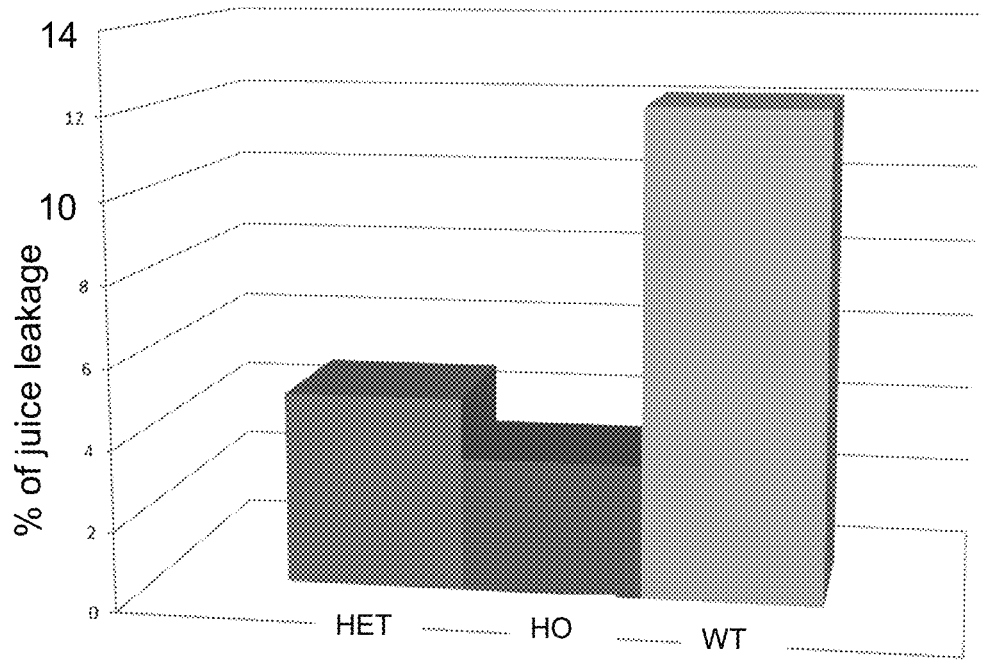

Juice leakage data for inner and outer parts of fresh fruits is shown in FIGS. 4 and 5, respectively. These figures show that both fruits homozygous (HO) and heterozygous (HET) for the mutant C1MBP17_2 allele of the invention have a similar juice leakage which is lower than that of wild type fruits. Especially 18 days post harvest. After 18 days, juice leakage of both HO and HET fruits is about 14% of WT fruits for the inner parts, while HET outer parts only have a juice leakage of 22% compared to WT; and HO outer parts only have a juice leakage of 17% of WT.

The total juice leakage of HET fresh fruits inner parts is about 38% of that of WT fruits (3.5 gr and 9.3 gr, respectively).

The total juice leakage of HO fresh fruits inner parts is about 24% of that of WT fruits (2.2 gr and 9.3 gr, respectively).

The total juice leakage of HET fresh fruits outer parts is about 36% of that of WT fruits (4.2 gr and 11.8 gr, respectively).

The total juice leakage of HO fresh fruits outer parts is about 19% of that of WT fruits (2.2 gr and 11.8 gr, respectively).

The invention claimed is:

1. A plant of the species *Citrullus lanatus* var. *lanatus* comprising one or more mutations in the wild-type *Citrullus lanatus* Mads Box Protein 17_2 (C1MBP 17_2) allele encoding a protein of SEQ ID NO: 1, wherein said mutant allele encodes a mutant protein wherein the amino acid at position 36 of SEQ ID NO: 1 is replaced by a different amino acid, and wherein said replaced amino acid results in a protein of reduced function or no function compared to wild type plants lacking the mutant allele.

2. The plant of claim 1, wherein the plant is homozygous for said mutant C1MBP 17_2 allele.

3. The plant according to claim 1, wherein the amino acid at position number 36 of SEQ ID NO: 1 is replaced by Phenylalanine.

4. The plant according to claim 1, wherein the plant is an inbred line or wherein the plant is a hybrid.

5. The plant according to claim 1, wherein no wild type C1MBP 17_2 allele encoding a wild type C1MBP 17_2 protein of SEQ ID NO: 1 is present in the plant.

6. The plant according to claim 1, comprising the C1MBP 17_2 allele encoding the mutant protein of SEQ ID NO: 4 as found in seed deposited under Accession No. NCIMB 42340.

7. Seed from which the plant according to claim 1 can be grown.

8. A plant cell, tissue or plant part of the plant according to claim 1, or a fruit harvested from a plant according to claim 1.

9. Food, food products or compositions comprising or consisting of fruits or fruit parts of claim 8.

10. A plant of the species *Citrullus lanatus* var. *lanatus* comprising one or more mutations in the wild-type *Citrullus lanatus* Mads Box Protein 17_2 (C1MBP 17_2) allele encoding a protein comprising at least 95% sequence identity to SEQ ID NO: 1, wherein said mutant allele encodes a mutant protein wherein the amino acid at position 36 of SEQ ID NO: 1 is replaced by a different amino acid, and wherein said replaced amino acid results in a protein of reduced function or no function compared to wild type plants lacking the mutant allele.

11. The plant according to claim 10, wherein no wild type C1MBP 17_2 allele encoding a wild type protein comprising at least 95% sequence identity to SEQ ID NO: 1 is present in the plant.

12. The plant of claim 10, wherein the plant is homozygous for said mutant C1MBP 17_2 allele.

13. Seed from which the plant according to claim 10 can be grown.

14. A plant cell, tissue or plant part of the plant according to claim 10, or a fruit harvested from a plant according to claim 10.

15. Food, food products or compositions comprising or consisting of fruits or fruit parts of claim 14.

16. The plant according to claim 10, wherein the amino acid at position number 36 of SEQ ID NO: 1 is replaced by Phenylalanine.

* * * * *

SEQUENCE LISTING

```
<160> NUMBER OF SEQ ID NOS: 6

<210> SEQ ID NO 1
<211> LENGTH: 227
<212> TYPE: PRT
<213> ORGANISM: Citrullus lanatus

<400> SEQUENCE: 1

Met Gly Arg Gly Lys Ile Glu Ile Lys Arg Ile Glu Asn Thr Thr Asn
1               5                   10                  15
```

Arg Gln Val Thr Phe Cys Lys Arg Arg Asn Gly Leu Leu Lys Lys Ala
            20                  25                  30

Tyr Glu Leu Ser Val Leu Cys Asp Ala Glu Val Ala Leu Ile Val Phe
        35                  40                  45

Ser Ser Arg Gly Arg Leu Tyr Glu Tyr Ser Asn Asn Ser Ile Lys Thr
50                  55                  60

Thr Ile Glu Arg Tyr Lys Lys Ala Cys Ser Asp Ser Ser Ala Thr Ser
65                  70                  75                  80

Ser Val Thr Glu Leu Asn Thr Gln Tyr Tyr Gln Gln Glu Ser Ala Lys
                85                  90                  95

Leu Arg Gln Gln Ile Gln Met Leu Gln Asn Ser Asn Ser Asn Leu Val
            100                 105                 110

Arg His Leu Met Gly Asp Ser Leu Ser Ala Leu Thr Val Lys Glu Leu
        115                 120                 125

Lys Gln Leu Glu Asn Arg Leu Glu Arg Gly Ile Thr Arg Ile Arg Ser
    130                 135                 140

Lys Lys His Glu Met Leu Leu Ala Glu Ile Glu Tyr Leu Gln Lys Arg
145                 150                 155                 160

Glu Ile Glu Leu Glu Asn Glu Asn Val Cys Ile Arg Thr Lys Ile Ala
                165                 170                 175

Glu Val Glu Arg Leu Gln Gln Ala Asn Met Val Ser Gly Gln Glu Leu
            180                 185                 190

Asn Ala Ile Gln Ala Leu Ala Ser Arg Asn Phe Phe Ser Pro Asn Met
        195                 200                 205

Met Glu Gly Gly Ala Val Thr Tyr Ser His Gln Asp Lys Lys Met Leu
    210                 215                 220

His Ile Gly
225

<210> SEQ ID NO 2
<211> LENGTH: 860
<212> TYPE: DNA
<213> ORGANISM: Citrullus lanatus

<400> SEQUENCE: 2
atggggagag gaaagattga aataaagaga atagaaaaca caacaaatcg acaagtgaca      60
ttctgcaaga gaagaaatgg acttttgaag aaagcttatg aactctctgt tctttgtgat     120
gctgaagttg ccctcattgt cttctccagc cgtggccgtc tctatgaata ctccaataac     180
agtatcaaaa ctactattga gaggtacaag aaggcttgtt ctgatagctc agctaccagc     240
tctgtcactg aactaaatac tcaatattat cagcaagaat cggctaagct gcgtcaacaa     300
atacaaatgc ttcagaattc aacagcaat cttgttaggc acttgatggg ggactccttg     360
agtgctctta cagtcaaaga actaaagcag cttgaaaata ggcttgaaag gggcatcact     420
agaatcagat caaagaagca tgaaatgttg ctagcagaaa ttgagtatct tcaaaaaagg     480
gagattgagc tggagaatga aaatgtgtgt attagaacca agatagctga agttgagagg     540
ctccaacaag caaacatggt atctggacaa gaactgaatg caattcaggc attggcttct     600
cgtaatttct tctctcctaa tatgatggaa ggtggagctg ttacttactc tcatcaagac     660
aagaagatgc ttcatattgg gtgatgattt gcagctgttt tggtgaccaa aatgatgggg     720
acaaatgttt gttttgatta ctattcagga aatcattgag attgcaaaaa aattaaaata     780
aaatatgccc atcattttgt gaagtaaaaa atttaattaa ttttacttaa tgatcaatga     840
tgatgatgat cagtgtgtga                                              860

<210> SEQ ID NO 3
<211> LENGTH: 10445
<212> TYPE: DNA
<213> ORGANISM: Citrullus lanatus

<400> SEQUENCE: 3

| | | | | | |
|---|---|---|---|---|---|
| ctaattctaa | ctcataattg | ttcaacaaaa | aacatcttct | aactcctata | ttatttctat | 60 |
| aacaatcatg | atatgacgta | tgcgtgaaag | aaaatataaa | gataaagatg | aatagagaag | 120 |
| aaacaattat | agaattatct | ttcacagagt | agtggaccac | gtggaagggt | atgatttatt | 180 |
| cgaaaataac | ttacacatat | aaccctaggt | ttgttataga | atctaaacat | caaaacacaa | 240 |
| taataaaaat | aaaataaaaa | aaaaaaaaaa | aaaaaaaaaa | aaagcaaaag | aggggttgat | 300 |
| gcaaaattaa | aattaaaagg | attagtgtgt | gggtattagg | tagattttgc | attaagtaaa | 360 |
| tgaaagaaa | ttgtgaagaa | ggagagaaag | gggcaaaaag | gtaaaataaa | aaaaatgaaa | 420 |
| gggaaagaaa | aaagtaaagg | aaagtattgc | tgattttggt | gggaatttgg | aaatgcagag | 480 |
| aagttttaat | tcagctataa | ctccaatgtc | ttgtatcagt | ttcaggcaaa | ctcccacttt | 540 |
| ctctctctct | tttctaaaat | atattgacag | atttccattc | agattttgta | tttttgagat | 600 |
| ttgcttacta | aagaagcttc | attttctttc | tacctttctt | aattttattg | gaaaattcat | 660 |
| ctcaaaccct | ccatttctct | aaggtttgtt | ttctttcttc | atcatttctt | caaaccccctc | 720 |
| taaccaaaaa | ttaaacccctt | ttcccatttt | tgttcatcat | ttagatctat | ctgttcaacc | 780 |
| catacaacta | aaatcatcat | catcttcttc | ttcttcttct | tcttcttctt | gcattctttt | 840 |
| gggtacccat | ttctcatgtt | ttgattcctt | caatatttt | tttttttttg | agttgaaaca | 900 |
| atataaatat | gattgtgtgt | atcgtatttt | atgtagttgt | tgggttgtat | ataaattaaa | 960 |
| ataatgaata | tttttcagga | agatatcaaa | agatcagtag | agaagatcga | tggggagagg | 1020 |
| aaagattgaa | ataagagaa | tagaaaacac | aacaaatcga | caagtgacat | tctgcaagag | 1080 |
| aagaaatgga | cttttgaaga | aagcttatga | actctctgtt | ctttgtgatg | ctgaagttgc | 1140 |
| cctcattgtc | ttctccagcc | gtggccgtct | ctatgaatac | tccaataaca | ggttaggttt | 1200 |
| ggttttttt | tttttttcct | ttttcttttc | tttttctttc | gttctccgat | ccgtgcaaca | 1260 |
| tttgaacctc | taaccttta | actaccgaac | cacccaaagt | gaggtgaaag | gagcatgtaa | 1320 |
| ttgcatcaac | actatattgt | gtttattaca | tgtgttttct | tttctctttt | aacaacaata | 1380 |
| cattatattt | aaccttcttt | aaattggaag | ttgcattgtg | gccgtcaccct | caagttttt | 1440 |
| tactttaaa | tttgttaata | aaaggatttc | taaacttatt | ctcaacttttt | aagaaatttg | 1500 |
| attccccaaa | atttaaaaaa | aaaaaaaaaa | aaaagttta | aaacgcgatc | atataaccct | 1560 |
| aaacattcat | ttaagtgtct | agtagatcta | tgaatttta | agaaaattgt | ttagacacac | 1620 |
| aattgaaaat | ccaaggacat | attatattga | cacaaaaatt | gaaattccaa | gaacaaatta | 1680 |
| aaagttaatt | acaaattgaa | tagactcact | aacacttgaa | attcactttc | aaaagaggtt | 1740 |
| gtctggaatg | gactaaattt | gtaatggtta | ttcctagaga | aagatgaaga | aagaatatgg | 1800 |
| tagaagtatg | aaaagaatgg | gcatatgaca | accaaaatcc | caatattgat | tgttggataa | 1860 |
| atattaaaaa | aaaagtgtgg | cttccttgta | tagttagatt | tatgaggcat | gagctgtttt | 1920 |
| tgatgaaaat | tttagtataa | aaatgtcaat | cttttttccaa | cagtgaaaga | actgttcatg | 1980 |
| gaacattaaa | aaggaataaa | aacaaaacaa | cctcttccca | cttcaaactc | aatgttccct | 2040 |
| tcatttctag | ggtttcaact | tccaacttgg | tccaaccttg | aaaaattaaa | aatcaattat | 2100 |

```
tcacaattttt atgaatatat atattttgtc ctcaagtttc aaaattttat gcatttagtt   2160
gtttaagttt tgagtttgat tttaatttag tttttaagtt ttaaaatgtc acaattttac   2220
ctttgaagtt tggaaatttt gtttcaattt tggtccttaa attttaagat ttatactttt   2280
aatcatggtt ttctttttt cattttttac taaatactca tttaagtctt ggtgttaatg   2340
tctattaatt aattaaaaaa attaaagaat tatattaatt aaatttcaca acttttttc   2400 atcgcattta aaactttact tcataattat cttaaattaa ttaatagtta aaaatcaaag   2460
ttaaaagtgt aaatcttgaa acgtatggac caaattgaaa caaaaattga atctcaagg   2520 gtaaaattgt aacatttgaa acttaatgac taaattgaaa tgaaaatcaa aacgcaaaga   2580
ttatatgtgt aacatttga atatagagac caaaaaagca ttttgtcaaa ttttatttc   2640 agtttatttt tttctatttt ccaaatcaga ccttttgatc tatgatgcaa tctaatctac   2700
ctttgaaaac agttaagctc aattttagaa cttaagaaaa atagttttct ttattaaaaa   2760
aaaaatcata tttgtttaaa attaaataaa taaagaattt gttggtggag taaactctaa   2820
agacagtttt gacccttttt tttttctgaa atgttttttt tcctcttatt atgtatcatc   2880
tgcacctctg ggcttggttt tgtgatttcc aagaacattt cccatttgtt tgggcttctg   2940
cgttcttgtg ttttttaact tttttaagaa tcagattatt gtctgtcaca gctttgcccc   3000
atcaatgttt ttataaacca taattatttt gaaattgtat aaattaaaat gtaaactaat   3060 aacaacttt gtaagtgttt caagttatat atatatatat atagtgttca ttatattcca   3120
tattaaacta tgagcagtag tattagttat ttatgtggag cttgagaaaa gcaagagtgt   3180
gaggtctgac aaaacaactt gaaacatggt tacaaagcat tttaaaatta taggactatt   3240
caaaactgtg ttttgcatat ccattttcc tcatcccctt tatgttttc cctcttgtg   3300 taaatatcca aacagaatct atagcccata caacattatt tatttattta tttatttatt   3360
tttaattcca tttttaagctc tttagtttgt tccaattccc catatctccc attttcttgc   3420
tatatctttt ctttcttcat ggggtttct tttcaaaatt caaagaaaaa ccctccaaaa   3480
acaaaagcca cttggtacca ttggatattc tgatgtcaac aaaatttaag ctcctgacat   3540 ggagatttt agggtttggt agagataaat taaatggaca ataccagaga ctagctatcc   3600
attatgtata tactaccact tacatattgt ttggaatatc gagaagagag aagaaaattc   3660
atatgtaaat ataccatttg atttttagg aacagaaaac tataaccaaa atcattttt   3720 aaccaaatct ttgttattca tatatttgct cacttgaaaa gtagattcga aacttaactt   3780
gtaaataaat ataatatatt atcattgtat aaatagattc attatcctct acataaaaat   3840
tctcatgtcc ttttaccatt tcttgtcttc ctgaattaat ctaggttttt aaaataaaat   3900
aaaataaaat aaaaaatcaa tcccactaat tgggcttttt caaactatat atgaactgta   3960 tctctttta agaattttt aatataattt tgtttactta tttacccttc aaatagggt   4020 atctgagtct tttctagggg tgtttggggc gttctataag ttggttatta tcattcgtgg   4080
gttacaagtg ttataatagt ttgtgtttgg gtgcaaatta ttttgtctt ggtcataata   4140 gattgtgttt ggggtataaa ttattttagt ttggatagga aatagtaaac atgataacaa   4200
agagagaaag agaggatgta ataaacatta taacgaatag taacattgta ccaaagagga   4260
atttgaaatc gtaataccgt agttaattat aattggagcc ccaaacatgg agtgagggct   4320
ataatagccc attccaccca cttgaagttg gagacccaaa catccccttc atttacttgg   4380
atgatcgttt cttaacttta ttagtgattc ttaaaattct atttatatat tgtaatatat   4440
```

```
attgagtgga agaatgaaac atttaacttt aaagtcgata atataagttg aatgaataaa      4500
tattacgttt gagtcttata attgaattga aggggtaaga tacccttgta tataggcttg      4560
ttatagaaca gtgatttatt catactagga ttaaaaaaag ctggccatct ggtattaaag      4620
gataaagaaa ttggactgat cagtattaaa taaaaattgt accatctgtt cagttatttc      4680
atcattttca tgacaaagct cagttcattg aaagaatctg tctaacatat atacatatac      4740
atattaggca ataattggaa gtgattttgc atctgcttat accatgaaca aaatcttggt      4800
gtcctatttt tttttaactt ttctaaagct tatttcccat ctacttgctc caaaataaaa      4860
ttctggatca aatttttttt tttttttgac agatcaattg ttttaggcat attgttagtt      4920 tttactttt acaaaactta ccaacttaat ccctccctt tcttttgtct gcatgatcac      4980
attattgtct gttaaatatg tttgacactc taattaattt aataatgtta tgcaaggtca      5040
cccatttctt aaatgatttt aaatcttagc ctaataggat ggtttgaaca aaaaccttaa      5100
cttggatgga aggtcatgtc aattactgcg agttaatctt gctttgactt gtagttataa      5160
aacgtttaac catttgtaat gattaaaagt gcaattaggt tttcctaaat tttataatca      5220
aagttaaggt ttcaaaactt gagaaattgg tagcaaaatt ttagtattaa aaacctaagc      5280
gagatggtta cacatctaca tgcaaattga gttaggtttg atttggcaat gccatattat      5340
agtattattt ggttccatgt catttaacta ttaattcaat tgatcattca acattaataa      5400
tgtgtcagta ttagttcctt gttgagtagt ttagatggta agaaagtgaa tgaatggtgt      5460
gtggtaatta agaatataat gttgatgaaa ggattagtag taaaatagtt attattatat      5520
gcagtatcaa aactactatt gagaggtaca agaaggcttg ttctgatagc tcagctacca      5580
gctctgtcac tgaactaaat actcaagtca gcttctctct ccctcatatt ttgagtctag      5640
tttctatttg atctcttggt tttaaaatat tacacttta tctctgaatt ttagtttcat      5700
ttttatttgg tccctaaata ttactcttga gttttgagtt tagttttttt accctcgaga      5760
gtaaaagtgt aacctttga aatctaagga ccaaatagaa attaaactct agtgtaacat      5820
tttgaaatct aaagaccaaa tcgaaactag atataaaacc taggtactaa aaagttgttt      5880
tttccattaa aaaaaaaaag aagaaaaaag aaaaagagag tttgtcattg aaagattgtg      5940
tgaagttctt aactaaatca tagagatgaa attgatatag gttttaaatt atgaaaacca      6000
aattgaaact atgcttaaac caaaaacaca aaatctctaa tcaatccaat ttttcaaatg      6060
aaaagctttg gtattttag aaattgtaca actttaaaat tattgtcgaa ttattttaa      6120 aagtttgaaa gtaaatttag gcattcaatt gagtattatc tagaagaagt gcaagaaaat      6180
atcacaaacg atgtacaata aattcataaa ataataacaa attaactaat tggtcttaat      6240
attcatgaag cctaacatgt tcttatgata tgtgacatga aaaaaaaaat gaagtattat      6300
cagcaagaat cggctaagct gcgtcaacaa atacaaatgc ttcagaattc caacaggtta      6360
ttattatttg taattttct ttaataccte attcatatgt atatattatt gggctaaata      6420
tataatttta tctttaatat tttctttttt ttcttttttt ttttcaatt tcatccctaa      6480 tttttaaacc aagttcatat agagtgttgt tcacaaaaga ttgttagggt atatttgttt      6540
tagctttaaa atcgttcaat tttgaaaaaa gtttgagtaa tcgcgaaaaa ataagtttat      6600
agaataggtt attttaagat aatcacttga aatcaacttt taggaaaatg atatcaaatt      6660
gattttccta atttgtataa ttatattaaa atgataaaaa cgtcctcaaa agtcatctat      6720
ctcaaattga aaaaaaaaaa ccattaatga aaatgaagaa taaaaaatac tttcagtata      6780
taacaaatca aacaaatttg tttcataaat tttttatat tacaattttg atgaaaagta      6840
```

```
tttaaatgaa ttttttatta tttttttttt ttttgaaagt cagagtccat tagttaagaa      6900
gtatttgaaa atatgctttt tattctgggg ttgggtgaag aacacactta ttttattatt      6960
atattaggga gaaaaaaaaa aaaaaaaaaa aagacagaaa gagagttaaa attcttttaa      7020
aatatatata tatatattaa acacataaaa gatggaaatt agggaggaaa ttagagaaaa      7080
gaaagaaaga aagaaatatt gaaagaaaaa aatgatatat ttagccatga aagaaagata      7140
tatttaaggt gggggttgaa taagctactc tcatttgttg aagcaatctt gttaggcact      7200
tgatggggga ctccttgagt gctcttacag tcaaagaact aaagcagctt gaaaataggc      7260
ttgaaagggg catcactaga atcagatcaa agaaggttaa ttcaattttc aatctaatta      7320
aataagttta atgaagaatc attacctctc tacaattata taattgtttt caaaacatac      7380
ttcaatctgc ttctttcttc aacagcatga aatgttgcta gcagaaattg agtatcttca      7440
aaaaagggta ttctacactt aaaccatctt atttcacata ttttaccgtt ttagactcgt      7500
ttgataatca tttcgacaaa ttttcttgtt aaataattga tgctattcct tgtatatagg      7560
agattgagct ggagaatgaa aatgtgtgta ttagaaccaa ggtatgtata cacatcaaac      7620
ttcatttctt gccectctgg taaattgaca tcttaaacta agtatcaaaa tccacaataa      7680
atccacgtca atctgaacat agtttaatag ataaagacaa cagttaccat ttcaataatt      7740
gatagtttaa tcttcacaac catttgtggg atgacattct tcttctgaca agccattgga      7800
atactacatc aaacatttt tttgtaatta tgatgccact accattgctt taaattggat       7860
ggctttcctt tgatttgcct ttgttttcgc cttagctttt gtatgagctt cactctagct      7920
cttgctgtaa ataacttctt ttatgaatgc atcgcttttg gctttggaac gtgatgaggg      7980
tgctacggtg gtgttaactt agttgagatg tcctgatgca cctagtgatc tctgtgatcc      8040
ccattagtat tttgttaaaa aaaaaaaaaa aaaaaaattg atagtttaat ctcatgtcac      8100
aattgttgga caaagaaaat ttggacatat caaccatttt tctttttatg cttttatatt      8160
ttacctagtt tgtttcgtca atttcttttc ctagttcaac aacatatagt tgttagaaat      8220
gactagccca tgaattgatc atgggtatat agatgaggat agttatttcc aatagtatga      8280
ggtcttttag gtggttctaa aagcaaagtt atgagagttt atgtcataag tggacaatat      8340
caatcatact attgtagaga taggtgtgag gattcaaaaa tagaatatat gtcttgacca      8400
attaagctat atatcgctaa gtttgcttgt atgtagttga tatatgaatg tctatccatg      8460
atatgtgtct tagccaattc agctatgctc aagttgacat attgaataaa aaattactaa      8520
agctatagct tcttaaaaaa agtagaattc acatcttaac tattaagtta ctattatgat      8580
agagagacct cacaagcttt caagatacac gtgttactcc tctcattaac atttgatttt      8640
gagataaaat ccgtattgat aaaatctcat ttagtttatt ctaaattcat atagtgacaa      8700
taatttcttg tgtgtggggg gttagatagc tgaagttgag aggctccaac aagcaaacat      8760
ggtatctgga caagaactga atgcaattca ggcattggct tctcgtaatt tcttctctcc      8820
taatatgatg gaaggtggag ctgttactta ctctcatcaa gacaagaaga tgcttcatat      8880
tgggtatttc tctccaactt tagtatataa taatttgagt ttctatactc taaactatcc      8940
aatgattttg tctctatcat aaataattat tgttaaaatt aaagactaca tctgtctatt      9000
cgctacaagg attaaatctt tacataataa acattcaaac atactttga tggaaaattt       9060 tctcaaattt aaaagtgtaa ttactaaatg gatacgaatt agattttata tagggactaa      9120
attgttactc gaatgaaagt taataaatca aaaatatgtg tttcttagaa ttaaaggttg      9180
```

```
aatgggataa aattaaaagt gatcaagact cttatgtttg aataggcaat gattttttt     9240 ttttttttccg cttctgatgc acaggtgatg atttgcagct gttttggtga ccaaaatgat    9300
ggggacaaat gtttgttttg attactattc aggaaatcat tgagattgca aaaaattaa    9360 aataaaatat gcccatcatt ttgtgaagta aaaaatttaa ttaattttac ttaatgatca    9420
atgatgatga tgatcagtgt gtgatgtgat ttgcagctgt gtgtgtttca aattatatat    9480
atattatata ctgcatacat atgatatgtg ctacatcgac tctaatgatg atgtgtaatt    9540
ctatgaatga ttcttgtgcc cacatggacc aataggaatg tgaaacttgt caactctaga    9600
gttttacttt tgatctcttt aaatattatt tgagttgaat aaataattta atatttatct    9660
cttattattt atatatataa aaaggcataa tgcaaaaata aattgaatga actttacaga    9720
gagagaataa ttaatattag tttttttttt aactaaacat taggcttgaa aaatctatcc    9780
tttttttttt gtttatgttt atttttttat taatatatta aatcagtgtg taatgaaggt    9840
gtcaagaatg tgttaaccta gttgagatat ttttgtacac ttaccgatcc ttgaatccct    9900
agttctaaaa aaatctcacc ctttatgttt ctgttttg tgattgagtc aagtcacctg      9960
tcaacattgc aaactagaag attaagaat gaaaatgtca cttttaaacc catgatgttt    10020
tgagatttta aatcattgaa ttaaattat ttaaaatgta ggtagaataa ttcatatttg    10080
ggacaagaat ttgggggaga tgtgttacct tttttttacc ttttttgca tttacatggg    10140 attttttac catttatttt attttgtact tattattttt ttaaccaaca ttagatatga    10200
gtaactaata ttcccaaaac atatgtcatg ggattccatt ttatttattt atttgttatt    10260
attattcaga aaattatttt aaattacaaa attatagaaa atatttacaa ataataacaa    10320
aatattacca tctatccgtg acagactgca atatactaca atctgtgtct atcatggtat   10380
agataacaca aaagtagtct attgtgatct atcgcaaata gacagtgaaa ttttgctata    10440
tttga                                                               10445
```

<210> SEQ ID NO 4
<211> LENGTH: 227
<212> TYPE: PRT
<213> ORGANISM: Citrullus lanatus

<400> SEQUENCE: 4

```
Met Gly Arg Gly Lys Ile Glu Ile Lys Arg Ile Glu Asn Thr Thr Asn
1               5                   10                  15

Arg Gln Val Thr Phe Cys Lys Arg Arg Asn Gly Leu Leu Lys Lys Ala
            20                  25                  30

Tyr Glu Leu Phe Val Leu Cys Asp Ala Glu Val Ala Leu Ile Val Phe
        35                  40                  45

Ser Ser Arg Gly Arg Leu Tyr Glu Tyr Ser Asn Asn Ser Ile Lys Thr
    50                  55                  60

Thr Ile Glu Arg Tyr Lys Lys Ala Cys Ser Asp Ser Ser Ala Thr Ser
65                  70                  75                  80

Ser Val Thr Glu Leu Asn Thr Gln Tyr Tyr Gln Glu Ser Ala Lys
                85                  90                  95

Leu Arg Gln Gln Ile Gln Met Leu Gln Asn Ser Asn Ser Asn Leu Val
            100                 105                 110

Arg His Leu Met Gly Asp Ser Leu Ser Ala Leu Thr Val Lys Glu Leu
        115                 120                 125

Lys Gln Leu Glu Asn Arg Leu Glu Arg Gly Ile Thr Arg Ile Arg Ser
    130                 135                 140
```

```
Lys Lys His Glu Met Leu Ala Glu Ile Glu Tyr Leu Gln Lys Arg
145                 150                 155                 160

Glu Ile Glu Leu Glu Asn Glu Asn Val Cys Ile Arg Thr Lys Ile Ala
                165                 170                 175

Glu Val Glu Arg Leu Gln Gln Ala Asn Met Val Ser Gly Gln Glu Leu
            180                 185                 190

Asn Ala Ile Gln Ala Leu Ala Ser Arg Asn Phe Phe Ser Pro Asn Met
        195                 200                 205

Met Glu Gly Gly Ala Val Thr Tyr Ser His Gln Asp Lys Lys Met Leu
    210                 215                 220

His Ile Gly
225

<210> SEQ ID NO 5
<211> LENGTH: 860
<212> TYPE: DNA
<213> ORGANISM: Citrullus lanatus

<400> SEQUENCE: 5
atggggagag gaaagattga aataaagaga atagaaaaca caacaaatcg acaagtgaca      60
ttctgcaaga gaagaaatgg acttttgaag aaagcttatg aactctttgt tctttgtgat     120
gctgaagttg ccctcattgt cttctccagc cgtggccgtc tctatgaata ctccaataac     180
agtatcaaaa ctactattga gaggtacaag aaggcttgtt ctgatagctc agctaccagc     240
tctgtcactg aactaaatac tcaatattat cagcaagaat cggctaagct gcgtcaacaa     300
atacaaatgc ttcagaattc aacagcaat cttgttaggc acttgatggg ggactccttg      360
agtgctctta cagtcaaaga actaaagcag cttgaaaata ggcttgaaag gggcatcact     420
agaatcagat caagaagca tgaaatgttg ctagcagaaa ttgagtatct tcaaaaaagg      480
gagattgagc tggagaatga aaatgtgtgt attagaacca gatagctga agttgagagg      540 ctccaacaag caaacatggt atctggacaa gaactgaatg caattcaggc attggcttct     600
cgtaatttct tctctcctaa tatgatggaa ggtggagctg ttacttactc tcatcaagac     660
aagaagatgc ttcatattgg gtgatgattt gcagctgttt tggtgaccaa atgatgggg      720 acaaatgttt gttttgatta ctattcagga atcattgag attgcaaaaa aattaaaata      780
aaatatgccc atcattttgt gaagtaaaaa atttaattaa ttttacttaa tgatcaatga     840
tgatgatgat cagtgtgtga                                                  860

<210> SEQ ID NO 6
<211> LENGTH: 10445
<212> TYPE: DNA
<213> ORGANISM: Citrullus lanatus

<400> SEQUENCE: 6
ctaattctaa ctcataattg ttcaacaaaa aacatcttct aactcctata ttatttctat      60
aacaatcatg atatgacgta tgcgtgaaag aaaatataaa gataaagatg aatagagaag     120
aaacaattat agaattatct ttcacagagt agtggaccac gtggaagggt atgatttatt     180
cgaaaataac ttacacatat aaccctaggt tgttataga atctaaacat caaacacaa       240 taataaaaat aaaataaaaa aaaaaaaaaa aaaaaaaaa aaagcaaaag agggttgat       300 gcaaaattaa aattaaaagg attagtgtgt gggtattagg tagattttgc attaagtaaa     360
tgaaaagaaa ttgtgaagaa ggagagaaag ggcaaaaag gtaaaataaa aaaaatgaaa      420
gggaaagaaa aagtaaagg aaagtattgc tgattttggt gggaatttgg aaatgcagag      480
```

-continued

```
aagtttttaat tcagctataa ctccaatgtc ttgtatcagt ttcaggcaaa ctcccacttt    540
ctctctctct tttctaaaat atattgacag atttccattc agattttgta tttttgagat    600
ttgcttacta aagaagcttc attttttcttc tacctttctt aatttttattg gaaaattcat   660 ctcaaaccct ccattttctct aaggtttgtt ttcttttcttc atcatttctt caaacccctc   720
taaccaaaaa ttaaacccctt ttcccatttt tgttcatcat ttagatctat ctgttcaacc   780
catacaacta aaatcatcat catcttcttc ttcttcttct tcttcttctt gcattctttt    840
gggtacccat ttctcatgtt ttgattcctt caatatttt ttttttttg agttgaaaca     900 atataaatat gattgtgtgt atcgtatttt atgtagttgt tgggttgtat ataaattaaa   960
ataatgaata ttttttcagga agatatcaaa agatcagtag agaagatcga tggggagagg   1020
aaagattgaa ataagagaaa tagaaaacac aacaaatcga caagtgacat tctgcaagag   1080
aagaaatgga cttttgaaga aagcttatga actctttgtt ctttgtgatg ctgaagttgc   1140
cctcattgtc ttctccagcc gtggccgtct ctatgaatac tccaataaca ggttaggttt   1200
ggtttttttt tttttttcct ttttctttc tttttctttc gttctccgat ccgtgcaaca   1260
tttgaacctc taacctttta actaccgaac cacccaaagt gaggtgaaag gagcatgtaa   1320
ttgcatcaac actatattgt gtttattaca tgtgttttct tttctcttt aacaacaata    1380 cattatattt aaccttcttt aaattggaag ttgcattgtg gccgtcacct caagttttt    1440 tacttttaaa tttgttaata aaaggatttc taaacttatt ctcaacttt aagaaatttg   1500 attccccaaa atttaaaaaa aaaaaaaaaa aaaagttta aaacgcgatc atataaccct    1560
aaacattcat ttaagtgtct agtagatcta tgaatttta agaaaattgt ttagacacac   1620
aattgaaaat ccaaggacat attatattga cacaaaaatt gaaattccaa gaacaaatta   1680
aaagttaatt acaaattgaa tagactcact aacacttgaa attcacttc aaaagaggtt   1740 gtctggaatg gactaaattt gtaatggtta ttcctagaga aagatgaaga aagaatatgg   1800
tagaagtatg aaaagaatgg gcatatgaca accaaaatcc caatattgat tgttggataa   1860
atattaaaaa aaaagtgtgg cttccttgta tagttagatt tatgaggcat gagctgtttt   1920
tgatgaaaat tttagtataa aaatgtcaat ctttttccaa cagtgaaaga actgttcatg   1980
gaacattaaa aaggaataaa aacaaaacaa cctcttccca cttcaaactc aatgttccct   2040
tcatttctag ggtttcaact tccaacttgg tccaaccttg aaaaattaaa aatcaattat   2100
tcacaatttt atgaatatat atattttgtc ctcaagtttc aaaattttat gcatttagtt   2160
gtttaagttt tgagtttgat tttaatttag ttttttaagtt ttaaaatgtc acaatttttac   2220 ctttgaagtt tggaaatttt gtttcaattt tggtccttaa attttaagat ttatactttt   2280
aatcatggtt ttcttttttt catttttttac taaatactca tttaagtctt ggtgttaatg   2340
tctattaatt aattaaaaaa attaaagaat tatattaatt aaatttcaca acttttttc   2400 atcgcattta aaactttact tcataattat cttaaattaa ttaatagtta aaaatcaaag   2460
ttaaaagtgt aaatcttgaa acgtatggac caaattgaaa caaaaattga aatctcaagg   2520
gtaaaattgt aacatttgaa acttaatgac taaattgaaa tgaaaatcaa aacgcaaaga   2580
ttatatgtgt aacattttga atatagagac caaaaaagca ttttgtcaaa ttttatttc    2640 agtttatttt tttctatttt ccaaatcaga ccttttgatc tatgatgcaa tctaatctac   2700
ctttgaaaac agttaagctc aattttagaa cttaagaaaa atagttttct ttattaaaaa   2760
aaaaatcata tttgttaaa attaaataaa taaagaattt gttggtggag taaactctaa    2820
```

```
agacagtttt gacccttttt tttttctgaa atgttttttt tcctcttatt atgtatcatc    2880
tgcacctctg ggcttggttt tgtgatttcc aagaacattt cccatttgtt tgggcttctg    2940
cgttcttgtg ttttttaact ttttaagaa tcagattatt gtctgtcaca gctttgcccc     3000
atcaatgttt ttataaacca taattatttt gaaattgtat aaattaaaat gtaaactaat    3060
aacaactttt gtaagtgttt caagttatat atatatatat atagtgttca ttatattcca    3120
tattaaacta tgagcagtag tattagttat ttatgtggag cttgagaaaa gcaagagtgt    3180
gaggtctgac aaaacaactt gaaacatggt tacaaagcat tttaaaatta taggactatt    3240
caaaactgtg ttttgcatat ccattttttcc tcatccccctt tatgttttc cctctttgtg    3300 taaatatcca aacagaatct atagcccata caacattatt tatttattta tttatttatt    3360
tttaattcca ttttaagctc tttagtttgt tccaattccc catatctccc attttcttgc    3420
tatatctttt ctttcttcat ggggttttct tttcaaaatt caagaaaaa ccctccaaaa     3480 acaaaagcca cttggtacca ttggatattc tgatgtcaac aaaatttaag ctcctgacat    3540
ggagattttt agggtttggt agagataaat taaatggaca ataccagaga ctagctatcc    3600
attatgtata tactaccact tacatattgt ttggaatatc gagaagagag aagaaaattc    3660
atatgtaaat ataccatttg atttttttagg aacagaaaac tataaccaaa atcattttttt   3720 aaccaaatct ttgttattca tatatttgct cacttgaaaa gtagattcga aacttaactt    3780
gtaaataaat ataatatatt atcattgtat aaatagattc attatcctct acataaaaat   3840
tctcatgtcc ttttaccatt tcttgtcttc ctgaattaat ctaggttttt aaaataaaat    3900
aaaataaaat aaaaaatcaa tcccactaat tgggctttttt caaactatat atgaactgta    3960 tctctttttta agaattttttt aatataattt tgtttactta tttaccccttc aaatagggt    4020 atctgagtct tttctagggg tgtttggggc gttctataag ttggttatta tcattcgtgg    4080
gttacaagtg ttataatagt ttgtgtttgg gtgcaaatta ttttttgtctt ggtcataata   4140 gattgtgttt ggggtataaa ttattttagt ttggatagga aatagtaaac atgataacaa    4200
agagagaaag agaggatgta ataaacatta taacgaatag taacattgta ccaaagagga    4260
atttgaaatc gtaataccgt agttaattat aattggagcc ccaaacatgg agtgagggct    4320
ataatagccc attccaccca cttgaagttg gagacccaaa catcccccttc atttacttgg    4380 atgatcgttt cttaactttta ttagtgattc ttaaaattct atttatatat tgtaatatat    4440
attgagtgga agaatgaaac atttaacttt aaagtcgata atataagttg aatgaataaa    4500
tattacgttt gagtcttata attgaattga aggggtaaga tacccttgta tataggcttg    4560
ttatagaaca gtgatttatt catactagga ttaaaaaaag ctggccatct ggtattaaag    4620
gataaagaaa ttggactgat cagtattaaa taaaaattgt accatctgtt cagttatttc    4680
atcattttca tgacaaagct cagttcattg aaagaatctg tctaacatat atacatatac    4740
atattaggca ataattggaa gtgattttgc atctgcttat accatgaaca aaatcttggt    4800
gtcctatttt tttttaactt ttctaaagct tatttcccat ctacttgctc caaaataaaa    4860
ttctggatca aattttttttt tttttttgac agatcaattg ttttaggcat attgttagtt    4920 tttactttttt acaaaactta ccaacttaat ccctccctttt tcttttgtct gcatgatcac    4980
attattgtct gttaaatatg tttgacactc taattaattt aataatgtta tgcaaggtca    5040
cccatttctt aaatgatttt aaatcttagc ctaataggat ggtttgaaca aaaaccttaa    5100
cttggatgga aggtcatgtc aattactgcg agttaatctt gctttgactt gtagttataa    5160
aacgtttaac catttgtaat gattaaaagt gcaattaggt tttcctaaat tttataatca    5220
```

```
aagttaaggt tcaaaactt gagaaattgg tagcaaaatt ttagtattaa aaacctaagc    5280
gagatggtta cacatctaca tgcaaattga gttaggtttg atttggcaat gccatattat    5340
agtattattt ggttccatgt catttaacta ttaattcaat tgatcattca acattaataa    5400
tgtgtcagta ttagttcctt gttgagtagt ttagatggta agaaagtgaa tgaatggtgt    5460
gtggtaatta agaatataat gttgatgaaa ggattagtag taaaatagtt attattatat    5520
gcagtatcaa aactactatt gagaggtaca agaaggcttg ttctgatagc tcagctacca    5580
gctctgtcac tgaactaaat actcaagtca gcttctctct ccctcatatt ttgagtctag    5640
tttctatttg atctcttggt tttaaaatat tacactttta tctctgaatt ttagtttcat    5700
ttttatttgg tccctaaata ttactcttga gttttgagtt tagttttttt accctcgaga    5760
gtaaaagtgt aacctttga atctaagga ccaaatagaa attaaactct agtgtaacat    5820
tttgaaatct aaagaccaaa tcgaaactag atataaaacc taggtactaa aaagttgttt    5880
tttccattaa aaaaaaaaag aagaaaaaag aaaaagagag tttgtcattg aaagattgtg    5940
tgaagttctt aactaaatca tagagatgaa attgatatag gttttaaatt atgaaaacca    6000
aattgaaact atgcttaaac caaaacaca aaatctctaa tcaatccaat ttttcaaatg    6060
aaaagctttg gtatttttag aaattgtaca actttaaaat tattgtcgaa ttattttaa    6120 aagtttgaaa gtaaatttag gcattcaatt gagtattatc tagaagaagt gcaagaaaat    6180
atcacaaacg atgtacaata aattcataaa ataataacaa attaactaat tggtcttaat    6240
attcatgaag cctaacatgt tcttatgata tgtgacatga aaaaaaaaat gaagtattat    6300
cagcaagaat cggctaagct gcgtcaacaa atacaaatgc ttcagaattc caacaggtta    6360
ttattatttg taattttct ttaatacctc attcatatgt atatattatt gggctaaata    6420
tataaattta tctttaatat tttctttttt ttctttttt tttttcaatt tcatccctaa    6480
ttttttaacc aagttcatat agagtgttgt tcacaaaaga ttgttagggt atattttgttt    6540 tagctttaaa atcgttcaat tttgaaaaaa gtttgagtaa tcgcgaaaaa ataagtttat    6600
agaataggtt attttaagat aatcacttga aatcaacttt taggaaaatg atatcaaatt    6660
gattttccta atttgtataa ttatattaaa atgataaaaa cgtcctcaaa agtcatctat    6720
ctcaaattga aaaaaaaaa ccattaatga aaatgaagaa taaaaaatac tttcagtata    6780
taacaaatca aacaaatttg tttcataaat ttttttatat tacaattttg atgaaaagta    6840
tttaaatgaa tttttatta tttttttttt ttttgaaagt cagagtccat tagttaagaa    6900
gtatttgaaa atatgctttt tattctgggg ttgggtgaag aacacactta ttttattatt    6960
atattaggga gaaaaaaaaa aaaaaaaaa aagacagaaa gagagttaaa attcttttaa    7020
aatatatata tatatattaa acacataaaa gatgaaaatt agggaggaaa ttagagaaaa    7080
gaaagaaaga aagaaatatt gaaagaaaaa aatgatatat ttagccatga aagaaagata    7140
tatttaaggt gggggttgaa taagctactc tcatttgttg aagcaatctt gttaggcact    7200 tgatgggga ctccttgagt gctcttacag tcaaagaact aaagcagctt gaaaataggc    7260
ttgaaagggg catcactaga atcagatcaa agaaggttaa ttcaattttc aatctaatta    7320
aataagttta atgaagaatc attacctctc tacaattata taattgtttt caaaacatac    7380
ttcaatctgc ttcttcttc aacagcatga aatgttgcta gcagaaattg agtatcttca    7440 aaaagggta ttctacactt aaaccatctt atttcacata ttttaccgtt ttagactcgt    7500
ttgataatca tttcgacaaa ttttcttgtt aaataattga tgctattcct tgtatatagg    7560
```

```
agattgagct ggagaatgaa aatgtgtgta ttagaaccaa ggtatgtata cacatcaaac    7620
ttcatttctt gccccctctgg taaattgaca tcttaaacta agtatcaaaa tccacaataa    7680
atccacgtca atctgaacat agtttaatag ataaagacaa cagttaccat ttcaataatt    7740
gatagtttaa tcttcacaac catttgtggg atgacattct tcttctgaca agccattgga    7800
atactacatc aaacattttt tttgtaatta tgatgccact accattgctt taaattggat    7860
ggctttcctt tgatttgcct ttgttttcgc cttagctttt gtatgagctt cactctagct    7920
cttgctgtaa ataacttctt ttatgaatgc atcgcttttg ctttggaac gtgatgaggg     7980 tgctacggtg gtgttaactt agttgagatg tcctgatgca cctagtgatc tctgtgatcc    8040
ccattagtat tttgttaaaa aaaaaaaaa aaaaaaattg atagtttaat ctcatgtcac     8100
aattgttgga caagaaaat ttggacatat caaccatttt tcttttatg cttttatatt      8160 ttacctagtt tgtttcgtca atttcttttc ctagttcaac aacatatagt tgttagaaat    8220
gactagccca tgaattgatc atgggtatat agatgaggat agttatttcc aatagtatga    8280
ggtcttttag gtggttctaa aagcaaagtt atgagagttt atgtcataag tggacaatat    8340
caatcatact attgtagaga taggtgtgag gattcaaaaa tagaatatat gtcttgacca    8400
attaagctat atatcgctaa gtttgcttgt atgtagttga tatatgaatg tctatccatg    8460
atatgtgtct tagccaattc agctatgctc aagttgacat attgaataaa aaattactaa    8520
agctatagct tcttaaaaaa agtagaattc acatcttaac tattaagtta ctattatgat    8580
agagagacct cacaagcttt caagatacac gtgttactcc tctcattaac atttgattt     8640 gagataaaat ccgtattgat aaaatctcat ttagtttatt ctaaattcat atagtgacaa    8700
taatttcttg tgtgtggggg gttagatagc tgaagttgag aggctccaac aagcaaacat    8760
ggtatctgga caagaactga atgcaattca ggcattggct tctcgtaatt tcttctctcc    8820
taatatgatg gaaggtggag ctgttactta ctctcatcaa gacaagaaga tgcttcatat    8880
tgggtatttc tctccaactt tagtatataa taatttgagt ttctatactc taaactatcc    8940
aatgattttg tctctatcat aaataattat tgttaaaatt aaagactaca tctgtctatt    9000
cgctacaagg attaaatctt tacataataa acattcaaac atactttga tggaaaattt     9060 tctcaaattt aaaagtgtaa ttactaaatg gatacgaatt agatttata tagggactaa     9120 attgttactc gaatgaaagt taataaatca aaaatatgtg tttcttagaa ttaaaggttg    9180
aatgggataa aattaaaagt gatcaagact cttatgtttg aataggcaat gattttttt     9240 ttttttccg cttctgatgc acaggtgatg atttgcagct gttttggtga ccaaaatgat     9300
ggggacaaat gtttgttttg attactattc aggaaatcat tgagattgca aaaaaattaa    9360
aataaaatat gcccatcatt ttgtgaagta aaaaatttaa ttaattttac ttaatgatca    9420
atgatgatga tgatcagtgt gtgatgtgat ttgcagctgt gtgtgtttca aattatatat    9480
atattatata ctgcatacat atgatatgtg ctacatcgac tctaatgatg atgtgtaatt    9540
ctatgaatga ttcttgtgcc cacatggacc aataggaatg tgaaacttgt caactctaga    9600
gttttacttt tgatctcttt aaatattatt tgagttgaat aaataattta atatttatct    9660
cttattattt atatatataa aaaggcataa tgcaaaaata aattgaatga actttacaga    9720
gagagaataa ttaatattag ttttttttt aactaaacat taggcttgaa aaatctatcc     9780
tttttttttt gtttatgttt attttttat taatatatta aatcagtgtg taatgaaggt     9840
gtcaagaatg tgttaaccta gttgagatat ttttgtacac ttaccgatcc ttgaatccct    9900
agttctaaaa aaatctcacc ctttatgttt cttgttttg tgattgagtc aagtcacctg     9960
```

```
tcaacattgc aaactagaag attaaagaat gaaaatgtca cttttttaacc catgatgttt    10020 tgagatttta aatcattgaa ttaaatttat ttaaaatgta ggtagaataa ttcatatttg    10080
ggacaagaat ttgggggaga tgtgttacct ttttttttacc ttttttttgca tttacatggg   10140 atttttttac catttatttt attttgtact tattattttt ttaaccaaca ttagatatga    10200
gtaactaata ttcccaaaac atatgtcatg ggattccatt ttatttattt atttgttatt    10260
attattcaga aaattatttt aaattacaaa attatagaaa atatttacaa ataataacaa    10320
aatattacca tctatccgtg acagactgca atatactaca atctgtgtct atcatggtat    10380
agataacaca aaagtagtct attgtgatct atcgcaaata gacagtgaaa ttttgctata    10440
tttga                                                                10445
```